United States Patent [19]
Arrhenius et al.

[11] Patent Number: 5,811,391
[45] Date of Patent: Sep. 22, 1998

[54] CYCLIC CS-1 PEPTIDOMIMETICS, COMPOSITIONS AND METHODS OF USING SAME

[75] Inventors: Thomas S. Arrhenius; Mariano J. Elices; Anna Tempczyk, all of San Diego, Calif.; Zhong-Li Zheng, Lexington, Mass.

[73] Assignee: Cytel Corporation, San Diego, Calif.

[21] Appl. No.: 483,077

[22] Filed: Jun. 7, 1995

Related U.S. Application Data

[63] Continuation-in-part of Ser. No. 296,241, Aug. 25, 1994, abandoned.

[51] Int. Cl.$^6$ .......................... A61K 38/12; C07K 5/103; C07K 7/06; C07K 7/08
[52] U.S. Cl. .......................... 514/11; 530/327; 530/328; 530/329; 530/330; 930/260
[58] Field of Search .......................... 930/260; 530/317, 530/327, 328, 329, 330; 514/9, 11

[56] References Cited

U.S. PATENT DOCUMENTS 5,169,833  12/1992  Hansen, Jr. et al. .......................... 514/17

FOREIGN PATENT DOCUMENTS

WO 92/00995  1/1992  WIPO .............................. C07K 7/00
WO 94/15958  7/1994  WIPO .............................. C07K 7/06

OTHER PUBLICATIONS

Komoriya, Akira et al., "The Minimal Essential Sequence for a Major Cell Type–Specific Adhesion Site (CS1) Within the Alternatively Spliced Type III Connecting Segment Domain of Fibronectin is Leucine–Aspartic Acid–Valine." *J. Biol. Chem.* 266:15075–15079 (1991).

Wayner, E.A. et al., "Activation–dependent Recognition by Hematopoietic Cells of the LDV Sequence in the V Region of Fibronectin." *J. Cell Biology* 116(2):489–497 (1990).

Cardarelli, Pina M et al., "Cyclic RGD Peptide Inhibits $\alpha_4\beta_1$ Interaction with Connecting Segment 1 and Vascular Cell Adhesion Molecule." *J. Biol. Chem.* 269:18668–18673 (1994).

Hart, Stephen L. et al., "Cell Binding and Internalization by Filamentous Phage Displaying a Cyclic Arg–Gly–Asp–containing Peptide." *J. Biol. Chem.* 269:12468–12474 (1994).

Koivunen, Erkki et al., "Isolation of Highly Specific Ligand for the $\alpha_5\beta_1$ Integrin from a Phage Display Library." *J. Cell Biol.* 124:373–380 (1994).

Mousa, Shaker A. et al., "Antiplatelet Efficacy and Specificity of DMP728, a Novel Platelet GPIIb/IIIa Receptor Antagonist." *Cardiology* 83:374–382 (1993).

Nowlin, Dawn M. et al., "A Novel Cyclic Pentapeptide Inhibits $\alpha_4\beta_1$ and $\alpha_5\beta_1$ Integrin–mediated Cell Adhesion." *J. Biol. Chem.* 268:20352–20359 (1993).

Pfaff, Martin et al., "Selective Recognition of Cyclic RGD Peptides of NMR Defined Conformation by $\alpha\text{IIb}\beta_3$, and $\alpha_5\beta_1$ Integrins." *J. Biol. Chem.* 269:20233–20238 (1994).

Gurrath, Marion et al., "Conformation/Activity Studies of Rationally Designed Potent Anti–Adhesive RGD Peptides." *Eur. J. Biochem.* 210:911–921 (1992).

Kamber, Bruno et al., "The Synthesis of Cystine Peptides by Iodine Oxidation of S–Trityl–cysteine and S–Acetamidomethyl–cysteine Peptides." *Helvetica Chimica Acta.* 63:899–915 (1980).

*Primary Examiner*—Jeffrey E. Russel
*Attorney, Agent, or Firm*—Campbell & Flores LLP

[57] ABSTRACT

The present invention contemplates a cyclic peptide that inhibits the binding between the VLA-4 receptor expressed on inflammatory leukocytes and the fibronectin CS-1 peptide expressed on endothelial cells that are involved in immunoinflammatory disease states. Pharmaceutical compositions containing a contemplated cyclic peptide and processes for treating immunoinflammatory conditions using a binding-inhibitory cyclic peptide are also disclosed.

27 Claims, 1 Drawing Sheet

CYCLIC CS-1 PEPTIDOMIMETICS, COMPOSITIONS AND METHODS OF USING SAME

This application is a continuation-in-part of application Ser. No. 08/296,241, filed Aug. 25, 1994, now abandoned, which is herein incorporated by reference.

DESCRIPTION

1. Technical Field

The present invention relates to binding of inflammatory cells to endothelial cells that express the CS-1 portion of fibronectin on their surfaces, and more particularly to the inhibition of that binding by cyclic peptidomimetic compounds of minimal length.

2. Background Art

The immune response relies on leukocyte trafficking and immune surveillance as one of the underpinnings of host defense. Not only does this immune surveillance allow leukocytes to recirculate through lymphoid tissues normally, but also permits rapid leukocyte recruitment and extravasation to adjacent tissues at sites of inflammation. The $\alpha 4\beta 1$ (CD49d/CD29, VLA-4) cell adhesion receptor is an active participant in these leukocyte trafficking functions [Hemler, *Ann. Rev. Immunol.*, 8:365–400 (1990); Hemler et al., *Immunol. Rev.*, 114:45–65 (1990)].

The VLA-4 integrin heterodimer was discovered independently by three research groups and identified as a surface antigen on lymphocytes [Sanchez-Madrid et al., *Eur. J. Immunol.*, 16:1343–1349 (1986); Clayberger et al., *J. Immunol.*, 138:1510–1514 (1987); Hemler et al., *J. Biol. Chem.*, 262:11478–11485 (1987)]. Within the integrin family, VLA-4 is unique on several counts: (i) in contrast to related members of the $\beta 1$ subfamily, VLA-4 is predominantly expressed on cells of the hematopoietic lineage [Hemler, *Ann. Rev. Immunol.*, 8:365–400 (1990)], and is functionally involved in cell-cell, as well as cell-extracellular matrix (ECM) adhesive interactions [Hemler, *Ann. Rev. Immunol.*, 8:365–400 (1990)]; (ii) despite sequence homology with other integrin $\alpha$ subunits, the $\alpha 4$ subunit stands apart from the two major structural clusters of $\alpha$ subunits because $\alpha 4$ lacks an inserted I-domain, and does not undergo post-translational cleavage near the transmembrane region [Hemler, *Ann. Rev. Immunol.*, 8:365–400 (1990); Hynes, *Cell*, 69:11–25 (1992)]; and (iii) $\alpha 4$ contains a trypsin-like cleavage site that results in cell type-specific surface expression of at least two different structural variants termed $\alpha 4$-150 and $\alpha 4$ 80/70 [Pulido et al., *FEBS Lett.*, 294:121–124 (1991); Teixido et al., *J. Biol. Chem.*, 267:1786–1791 (1992); Rubio et al., *Eur. J. Immunol.*, 22:1099–1102 (1992)].

The VLA-4 integrin appears to be one of the earliest adhesion receptors found on CD34-expressing hematopoietic stem cells [Teixido et al., *J. Clin. Invest.*, 90:358–367 (1992)]. However, VLA-4 is expressed only on mature T and B lymphocytes, natural killer (NK) cells, monocytes, basophils and eosinophils, but not on erythrocytes, platelets and neutrophils [Hemler, *Ann. Rev. Immunol.*, 8:365–400 (1990); Gismondi et al., *J. Immunol.*, 146:384–392 (1991); Walsh et al., *J. Immunol.*, 146:3419–3423 (1991); Bochner et al., *J. Exp. Med.*, 173:1553–1556 (1992); Dobrina et al., *J. Clin. Invest.*, 88:20–26 (1991); Weller et al., *Proc. Natl. Acad. Sci. USA*, 88:7430–7433 (1991)].

To date, most adhesion functions mediated by VLA-4 can be explained by a direct molecular interaction between the VLA-4 integrin and either of two separate counterreceptor structures, namely, the cytokine-inducible vascular cell adhesion molecule-1 (VCAM-1) [Elices et al., *Cell*, 60:577–584 (1990); Rice et al., *J. Exp. Med.*, 171:1369–1374 (1990); Schwartz et al., *J. Clin. Invest.*, 85:2019–2022 (1990); Carlos et al., *Blood*, 76:965–970 (1990)], and a subset of the ubiquitous ECM protein fibronectin [Wayner et al., *J. Cell Biol.*, 109:1321–1330 (1989); Guan et al., *Cell*, 60:53–61 (1990); Ferreira et al., *J. Exp. Med.*, 171:351–356 (1990); Elices et al., *Cell*, 60:577–584 (1990)].

VCAM-1 is a member of the immunoglobulin (Ig) gene superfamily [Osborn et al., *Cell*, 59:1203–1211 (1989); Rice et al., *Science*, 246:1303–1306 (1989)] that is expressed predominantly in vascular endothelium in response to pro-inflammatory cytokines such as IL-1,TNF$\alpha$, and IL-4 [Osborn et al., *Cell*, 59:1203–1211 (1989); Rice et al., *Science*, 246:1303–1306 (1989); Thornhill et al., *J. Immunol.*, 145:865–872 (1990); Masinovsky et al., *J. Immunol.*, 145:2886–2895 (1990); Thornhill et al., *J. Immunol.*, 146:592–598 (1991); Schleimer et al., *J. Immunol.*, 148:1086–1092 (1992); Birdsall et al., *J. Immunol.*, 148:2717–2723 (1992); Swerlick et al., *J. Immunol.*, 149:798–705 (1992); Briscoe et al., *J. Immunol.*, 149:2954–2960 (1992)]. The VLA-4 binding sites on VCAM-1 have been mapped to the outermost N-terminal (first) Ig-like region of the 6-Ig-like domain VCAM-1 isoform [Taichman et al., *Cell Regul.*, 2:347–355 (1991); Vonderheide et al., *J. Exp. Med.*, 175:1433–1442 (1992); Osborn et al., *J. Exp. Med.*, 176:99–107 (1992)], and the first and fourth N-terminal Ig-like regions of the 7-Ig-like domain VCAM-1 isoform [Vonderheide et al., *J. Exp. Med.*, 175:1433–1442 (1992); Osborn et al., *J. Exp. Med.*, 176:99–107 (1992)]. Discrete amino acid sequences within the two separate Ig-like domains in VCAM-1 recognized by the VLA-4 integrin remain to be defined.

In contrast, a high affinity peptide recognition sequence for VLA-4 within fibronectin (FN) has been identified [Wayner et al., *J. Cell. Biol.*, 109:1321–1330 (1989); Ferreira et al., *J. Exp. Med.*, 171:351–356 (1990); Guan et al., *Cell*, 60:53–61 (1990); Mould et al., *J. Biol. Chem.*, 265:4020–4024 (1990); Garcia-Pardo et al., *J. Immunol.*, 144:3361–3366 (1990); Komoriya et al., *J. Biol. Chem.*, 266:15075–15079 (1991)]. That sequence comprises a 25-amino acid residue stretch, termed CS-1 [Humphries et al., *J. Cell Biol.*, 103:2637–2647 (1986); Humphries et al., *J. Biol. Chem.*, 262:6886–6892 (1987)].

The FN gene contains three separate exons termed EIIIA, EIIIB and V or IIICS, which are subject to alternative splicing [Hynes, "Fibronectin", Springer-Verlag, New York (1990)]. The presence of additional acceptor and donor splice signals within the IIICS region permits generation of increased diversity in FN by virtue of multiple IIICS polypeptide variants, for instance, five in human FN [Vibe-Pedersen et al., *FEBS Lett.*, 207:287–291 (1987); Hershberger et al., *Mol. Cell. Biol.*, 10:662–671 (1990)]. Consequently, only a subset of these molecular variants expresses the 25-amino acid residue CS-1 sequence recognized by VLA-4 [Wayner et al., *J. Cell. Biol.*, 109:1321–1330 (1989); Guan et al., *Cell*, 60:53–61 (1990)].

A minimal essential sequence for specific VLA-4 recognition of CS-1 has been identified as the tripeptide Leu-Asp-Val (LDV) [Komoriya et al., *J. Biol. Chem.*, 266:15075–15079 (1991); Wayner et al., *J. Cell. Biol.*, 116:489–497 (1992); Wayner WO 91/03252 published Mar. 21, 1991; Wayner WO 93/12809 published Jul. 8, 1993; and Humphries WO 92/13887, published Aug. 20, 1992] albeit VLA-4 binds to LDV with at least two orders of magnitude lower affinity than to the native CS-1 25-mer.

Nowlin et al., *J. Biol. Chem.*, 268(1):20352–20359 (1993) recently described a cystine-linked cyclic pentapeptide said to inhibit binding by both the Arg-Gly-Asp (RGD) and CS-1 regions of fibronectin to VLA-5 and VLA-4, respectively. That cyclic pentamer included the unnatural residue, thioproline (ThioP), and can be represented by Arg-Cys*-Asp-(ThioP)-Cys*(SEQ ID NO.1), that is cyclized through a disulfide bond formed at the starred cysteine residues.

VLA-4 shares with other members of the β1 integrin subfamily the ability to promote binding and penetration of microbial pathogens into mammalian cells. Thus, specific interactions of β1 integrins with the bacterial protein invasin [Isberg et al., *Cell*, 60:861–871 (1990); Ennis et al., *J. Exp. Med.*, 177:207–212 (1993)], as well as the protozoan *Trypanosoma cruzi* [Fernandez et al., *Eur. J. Immunol.*, 23:552–557 (1993)] have been described.

A multitude of in vitro studies suggest interactions of VLA-4 with its two known ligands, VCAM-1 and CS-1 FN, have profound biological significance. For instance, VLA-4 binding to VCAM-1 has been demonstrated in adhesion to cytokine-stimulated vascular endothelium by lymphocytes [Elices et al., *Cell*, 60:577–584 (1990); Rice et al., *J. Exp. Med.*, 171:1369–1374 (1990); Schwartz et al., *J. Clin. Invest.*, 85:2019–2022 (1990); Carlos et al., *Blood*, 76:965–970 (1990); Shimizu et al., *J. Cell Biol.*, 113:1203–1212 (1991)], monocytes [Carlos et al., *Blood*, 77:2266–2271 (1991); Jonjic et al., *J. Immunol.*, 148:2080–2083 (1992)], natural killer (NK) cells [Allavena et al., *J. Exp. Med.*, 173:439–448 (1991)], and eosinophils [Walsh et al., *J. Immunol.*, 146:3419–3423 (1991); Bochner et al., *J. Exp. Med.*, 173:1553–(1992); Dobrina et al., *J. Clin. Invest.*, 88:20–26 (1991); Weller et al., *Proc. Natl. Acad. Sci. USA*, 88:7430–7433 (1991)]. Because of its involvement in mediating leukocyte-endothelial attachment, VLA-4/VCAM-1 interactions are considered key in inflammation.

The VLA-4/CS-1 interaction, in turn, has been widely documented in hematopoiesis where adhesive interactions between hematopoietic progenitors expressing VLA-4 [Hemler et al., *Immunol. Rev.*, 114:45–65 (1990); Williams et al., *Nature*, 352:438–441 (1991); Roldan et al., *J. Exp. Med.*, 175:1739–1747 (1992); Sawada et al., *J. Immunol.*, 149:3517–3524 (1992); Wadsworth et al., *J. Immunol.*, 150:847–857 (1993)] and their ECM microenvironment play a critical role in precursor maturation and differentiation. Thus, CS-1 peptides have been shown to inhibit (i) attachment of murine hematopoietic stem cells to ECM derived from bone marrow stroma [Williams et al., *Nature*, 352:438–441 (1991)], (ii) immunoglobulin secretion by bone marrow-derived B cell progenitors [Roldan et al., *J. Exp. Med.*, 175:1739–1747 (1992)], (iii) bursal and postbursal development of chicken B cells [Palojoki et al., *Eur. J. Immunol.*, 23:721–726 (1993)], and (iv) thymocyte adhesion and differentiation induced by thymic stromal cell monolayers [Utsumi et al., *Proc. Natl. Acad. Sci. USA*, 88:5685–5689 (1991); Sawada et al., *J. Immunol.*, 149:3517–3524 (1992)]. VLA-4/CS-1 may also be involved in embryonic development, because CS-1 peptides have been shown to interfere with migration of avian neural crest cells [Dufour et al., *EMBO J.*, 7:2661–2671 (1988)].

In addition to VCAM-1, FN and CS-1 have also been implicated in the pathology of rheumatoid arthritis (RA) [Laffon et al., *J. Clin. Invest.*, 88:546–552 (1992)]. A role for the CS-1 splicing variant of FN has been established in mediating migration of inflammatory cells such as eosinophils across endothelial cell monolayers of VLA-4-expressing leukocytes [Kuijpers et al., *J. Exp. Med.*, 178:279–284 (1993)]. Recent studies have also documented that the expression of the CS-1 variant of FN is increased in human patients whose bodies reject transplanted kidneys.

The vast body of work suggesting that VLA-4 plays a role in leukocyte trafficking and inflammation has been largely confirmed by in vivo studies using anti-VLA-4 antibodies in various animal models. Essentially, the skin, brain, kidney, lung and gut are targets of a wide variety of VLA-4-dependent inflammatory reactions mostly resulting from recruitment of mononuclear leukocytes and eosinophils.

More specifically, these in vivo studies are as follows: contact hypersensitivity (CH) and delayed type hypersensitivity (DTH) in the mouse and rat [Ferguson et al., *Proc. Natl. Acad. Sci. USA*, 88:8072–8076 (1991); Issekutz, *Cell Immunol.*, 138:300–312 (1991); Issekutz, *J. Immunol.*, 147:4178–418 (1991); Elices et al., *Clin. Exp. Rheumatol.*, 11:S77–80 (1993); Ferguson et al., *Proc. Natl. Acad. Sci. USA*, 88:8072–8076 (1991); Chisholm, et al., *Eur. J. Immunol.*, 23:682–688 (1993)]; experimental autoimmune encephalomyelitis (EAE) in the mouse and rat [Yednock et al., *Nature*, 356:63–66 (1992); Baron et al., *J. Exp. Med.*, 177:57–68 (1993)]; nephrotoxic nephritis in the rat [Mulligan et al., *J. Clin. Invest.*, 91:577–587 (1993)]; passive cutaneous anaphylaxis in the guinea pig [Weg et al., *J. Exp. Med.*, 177:561–566 (1993)]; immune complex-induced lung injury in the rat [Mulligan et al., *J. Immunol.*, 150:2401–2406 (1993); Mulligan et al., *J. Immunol.*, 150:2407–2417 (1993)], spontaneous colitis in the monkey [Poldolsky et al., *J. Clin. Invest.*, 92:372–380 (1993)] and asthma in sheep [Lobb, WO 92/13798 published Jul. 22, 1993 ].

Thus, a preliminary conclusion from in vivo results is that VLA-4 contributes to inflammatory responses that emulate chronic conditions in humans. In an in vivo model of murine contact hypersensitivity, the CS-1 peptide partially inhibited recruitment of T lymphocytes to skin inflammatory sites [Ferguson et al., *Proc. Natl. Acad. Sci. USA*, 88:8072–8076 (1991)]. Because the Arg-Gly-Asp peptide from the cell adhesion domain of FN was also inhibitory in this animal model, the authors concluded that emigration of immune T cells to sites of antigenic challenge in the tissue could be facilitated by the interaction of leukocyte integrins with ECM proteins such as FN [Ferguson et al., *Proc. Natl. Acad. Sci. USA*, 88:8072–8076 (1991)].

In a more recent study, Elices and coworkers [Elices et al., *Clin. Exp. Rheumatol.*, 11:S77–80 (1993)] were unable to reproduce inhibition of contact hypersensitivity with the native CS-1 peptide. Instead, they found that the CS-1 peptide was rapidly cleared from blood circulation by proteolytic degradation.

Although CS-1 and VCAM-1 both bind to VLA-4, and an aspartic acid appears to be an important residue for binding to VLA-4 in each sequence, the remaining residues involved in binding to VLA-4 and the configuration of the peptides needed for binding differ. [Elices et al., *Cell*, 60:577–584 (1990); Masumoto et al., *J. Biol. Chem.*, 268:228–234 (1993)]. Thus, a CS-1 peptide that itself binds well to VLA-4 may not inhibit binding by VCAM-1, and vice versa.

The role of VLA-4 and the CS-1 peptide in various chronic and acute immunoinflammatory disease states having been established, it would be of importance if compounds could be found that inhibit the VLA-4-lymphocyte interaction and were other than anti-VLA-4 antibodies that can themselves induce an immune response on repeated administration or the CS-1 peptide that is large and costly to make, and also is subject to rapid degradation. The disclosure that follows describes such small molecules that are more potent than is CS-1 itself.

BRIEF SUMMARY OF THE INVENTION

The present invention contemplates a cyclic CS-1 peptidomimetic inhibitor peptide, compositions and methods (processes) for using such an inhibitor peptide.

A contemplated cyclic peptide corresponds in sequence to formula I:

$$R\text{-}Xaa^1\text{-}Z\text{-}Asp\text{-}Phe\text{-}Y\text{-}Xaa^2 \qquad I$$

wherein

R is
 (a) $R^1$ that is (i) absent so that the peptide is terminated by the free α-amine of Xaa or (ii) a $C_1$–$C_4$ acyl moiety, or
 (b) $R^2$ that is selected from the group consisting of phenylacetyl, benzoyl, phenylalanyl, tyrosyl, N-$C_1$–$C_4$ acyl phenylalanyl and N-$C_1$–$C_4$ acyl tyrosyl;
 the $Xaa^1$ and $Xaa^2$ groups are α-amino acid residues that together form a sulfide or disulfide bond in a chain that contains 3 to about 6 atoms, including at least one sulfur atom between the α-carbons of the two Xaa groups, and in which $Xaa^2$ has a C-terminal carboxamide group, or the C-terminal carboxyl is replaced by hydrogen. Preferably, at least one of $Xaa^1$ and $Xaa^2$ is an oxidized cysteine and the other is an oxidized cysteine, homocysteine or penicillamine residue such that the two Xaa's together form a disulfide bond, and $Xaa^2$ has a C-terminal carboxamide group.

Z is absent, or a peptide selected from the group consisting of Pro-Glu-Leu, Phe-Leu, Glu-Phe-Leu, Pro-Glu-Phe-Leu (SEQ ID NO:2), and Gly-Pro-Glu-Phe-Leu (SEQ ID NO:3); and Y is absent, Pro, or $Y^1$ that is a peptide selected from the group consisting of Pro-Ser, Pro-Ser-Thr and Pro-Ser-Thr-Val (SEQ ID NO:4);

with the provisos that:
 (i) R is $R^2$ when Z is absent, and
 (ii) $R^2$ is selected from the group consisting of phenylacetyl, benzoyl, N-$C_1$–$C_4$ acyl phenylalanyl and N-$C_1$–$C_4$ acyl tyrosyl when the two Xaa residues are separated by two amino acid residues.

A cyclic peptide of formula I, and formulas II and III hereinafter, is water-soluble and inhibits the binding of Jurkat cells (ATCC TIB 152) to a solid phase-bound peptide of SEQ ID NO:5 in an in vitro assay in an aqueous buffer at a pH value of 7.2–7.4 to an extent that is about 5- to about 600-fold better than the inhibition in the binding exhibited by a peptide of (SEQ ID NO:6).

In a more preferred embodiment, the cyclic peptide corresponds in sequence to formula Ia, shown below, $$R\text{-}Xaa\text{-}Z\text{-}Asp\text{-}Phe\text{-}Y\text{-}Xaa\text{-}NH_2 \qquad Ia$$

wherein

R is
 (a) $R^1$ that is (i) absent so that the peptide is terminated by the free α-amine of Xaa or (ii) a $C_1$–$C_4$ acyl moiety, or
 (b) $R^2$ that is selected from the group consisting of phenylacetyl, phenylalanyl and N-$C_1$–$C_4$ acyl phenylalanyl;
 at least one Xaa is an oxidized cysteine and the other Xaa is an oxidized cysteine, homocysteine or penicillamine residue such that the two Xaa's together form a disulfide bond;

Z is absent, or a peptide selected from the group consisting of Pro-Glu-Leu, Phe-Leu, Glu-Phe-Leu, Pro-Glu-Phe-Leu (SEQ ID NO:2), and Gly-Pro-Glu-Phe-Leu (SEQ ID NO:3); and Y is absent, Pro, or $Y^1$ that is a peptide selected from the group consisting of Pro-Ser, Pro-Ser-Thr and Pro-Ser-Thr-Val (SEQ ID NO:4);

with the provisos that:
 (i) R is $R^2$ when Z is absent, and
 (ii) $R^2$ is phenylacetyl or N-$C_1$–$C_4$ acyl phenylalanyl when the two Xaa residues are separated by two amino acid residues; i.e., when both Z and Y are absent.

In a still more preferred embodiment, the cyclic peptide corresponds in sequence to formula II, below, $$R\text{-}Xaa\text{-}Z^1\text{-}Asp\text{-}Phe\text{-}Y^2\text{-}Xaa\text{-}NH_2 \qquad II$$

wherein

R is
 (a) $R^1$ that is (i) absent so that the peptide is terminated by the free α-amine of Xaa or (ii) a $C_1$–$C_4$ acyl moiety, or
 (b) $R^2$ that is selected from the group consisting of phenylacetyl, phenylalanyl and N-$C_1$–$C_4$ acyl phenylalanyl;
 at least one Xaa is an oxidized cysteine and the other Xaa is an oxidized cysteine, homocysteine or penicillamine residue such that the two Xaa's together form a disulfide bond;

$Z^1$ is absent or Phe-Leu; and $Y^2$ is absent, Pro, Pro-Ser or Pro-Ser-Thr;

with the provisos that:
 (i) R is $R^2$ when Z is absent, and
 (ii) $R^2$ is phenylacetyl or N-$C_1$–$C_4$ acyl phenylalanyl when the two Xaa residues are separated by two amino acid residues.

A still more preferred cyclic peptide corresponds in sequence to formula III, below, $$R^1\text{-}Cys\text{-}Phe\text{-}Leu\text{-}Asp\text{-}Phe\text{-}Y^3\text{-}Cys\text{-}NH_2,$$

wherein
 the two Cys residues are oxidized to form a cystine residue;
 $R^1$ is (i) a $C_1$–$C_4$ acyl moiety or (ii) absent so that the peptide is terminated by the free α-amine of the oxidized Cys residue; and
 $Y^3$ is Pro or Pro-Ser.

The presently most preferred peptide has the sequence N-phenylacetyl-Cys-Asp-Phe-Cys-$NH_2$ (SEQ ID NO:7) in which the two cysteines are oxidized to form a disulfide bond-containing cystine residue.

A pharmaceutical composition containing an above cyclic inhibitor peptide is also contemplated. Such a composition contains the peptide dissolved or dispersed in a pharmaceutically acceptable diluent that is preferably aqueous. The peptide is present in the composition in an inflammation-reducing amount. That amount is also sometimes referred to herein as a CS-1/or sVCAM-1/VLA-4-inhibiting amount. An above-discussed more preferred, still more preferred or most preferred peptide is utilized in a more preferred, still more preferred or most preferred composition.

A process for treating fibronectin CS-1/or sVCAM-1/VLA-4-mediated inflammation is also contemplated. That process comprises administering to a mammal having that inflammation or otherwise in need of such a treatment as for prophylactic purposes, an inflammation-reducing amount of a before-described cyclic inhibitor peptide. Use of a more preferred, still more preferred or most preferred inhibitor peptide is more, still more or most preferred in this process. The cyclic inhibitor peptide is preferably administered in a before-described pharmaceutical composition.

All peptide formulas or sequences shown herein are written from left to right and in the direction from amino-terminus to carboxy-terminus. The abbreviations used herein for derivatives and residues of the twenty natural amino acids are reproduced in the following Table of Correspondence:

TABLE OF CORRESPONDENCE

| Abbreviation | | |
|---|---|---|
| 1-Letter | 3-Letter | Amino Acid |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| w | Trp | tryptophan |
| R | Arg | arginine |
| D | Asp | aspartic acid |
| N | Asn | asparagine |
| C | Cys | cysteine |
| X | Xaa | another residue, or one of several residues |

Alternatively, the cyclic inhibitor peptide of the present invention can be described as molecular formula. A preferred cyclic inhibitor peptide has the following formula:

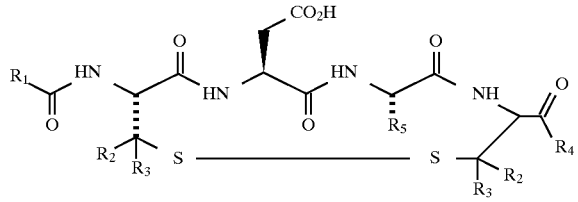

where $R_1$, is a phenyl or pyridyl group connected by a lower alkyl. $R_2$ is a H or methyl group. $R_3$ is a H or methyl group. $R_4$ is an amine, lower alkyl amine, lower alkyl ester or hydroxyl group. $R_5$ is a phenyl, pyridyl or cyclohexane group connected by a lower alkyl. A lower alkyl is one to five carbon atoms long.

The present invention has several benefits and advantages.

One salient benefit is that a cyclic inhibitor peptide contemplated here is more potent in inhibiting the VLA-4/CS-1 or the VLA-4/sVCAM-1 binding interaction than is CS-1 itself.

An advantage of the invention is that a contemplated cyclic inhibitor peptide also inhibits binding between VLA-4 and VCAM-1 to a greater extent than does a straight chain peptide that exhibits similar binding inhibition between VLA-4 and a CS-1 peptide.

Another advantage of the invention is that a contemplated cyclic inhibitor peptide is a relatively small molecule that is easily prepared in high purity.

Still further benefits and advantages of the invention will become apparent to the skilled worker from the disclosure that follows.

BRIEF DESCRIPTION OF THE DRAWINGS

In the drawings forming a portion of this disclosure.

DETAILED DESCRIPTION OF THE INVENTION

Figure 1:
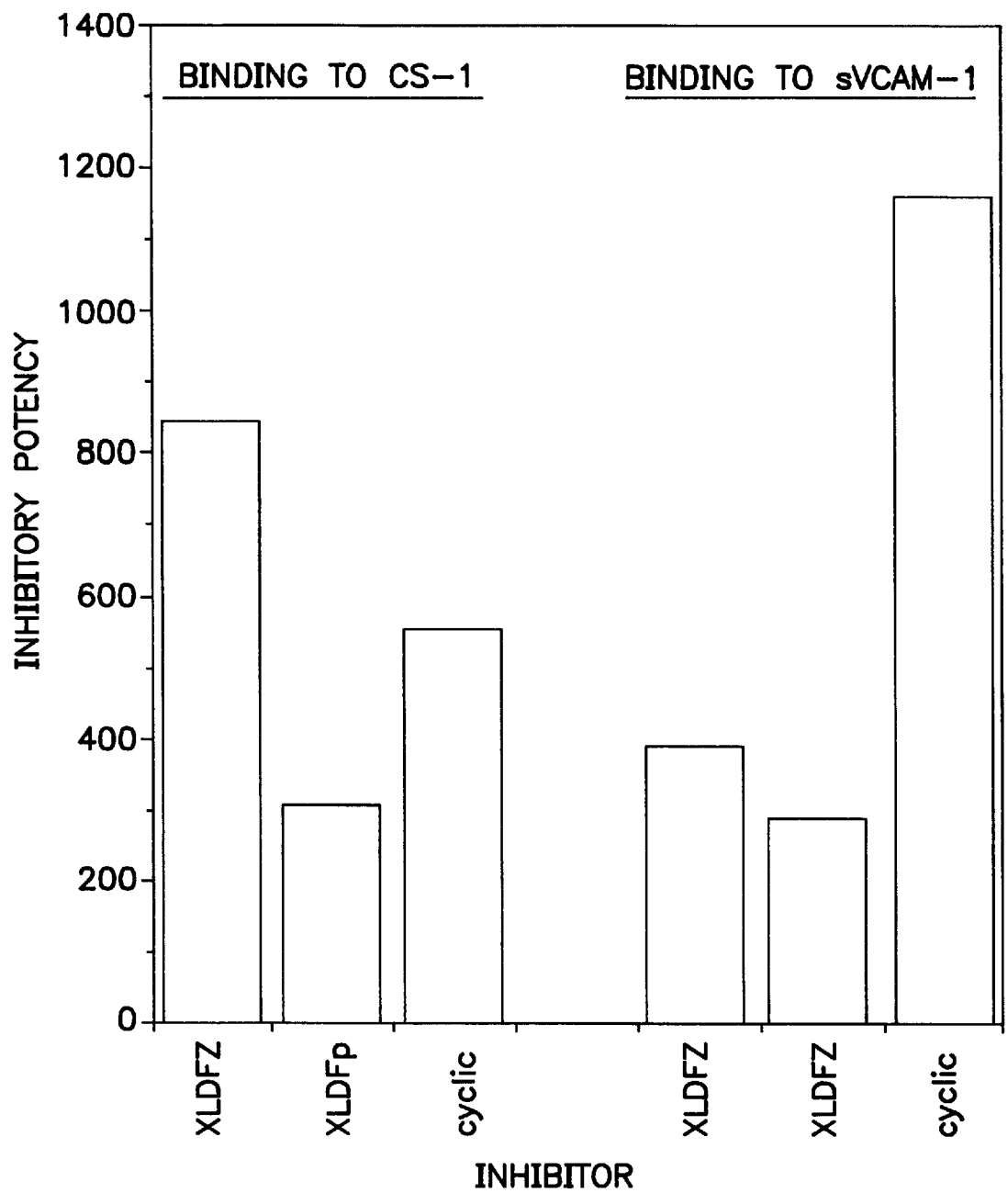
FIG. 1 is a graph illustrating the relative in vitro inhibition of binding of VLA-4-bearing Jurkat cells to the solid phase-bound CS-1 peptide (SEQ ID NO:5) on the left or soluble (s) sVCAM-1 on the right caused by straight chain peptides φAc-LeuAspPhe-morpholinamide (XLDFZ), φAc-LeuAspPhe-D-Pro-NH$_2$ (XLDFp) or the disulfide-containing cyclic peptide CysAspheCys-NH$_2$ (cyclic; SEQ ID NO:8), respectively. Inhibitions on the left are relative to the inhibition provided by the "standard" peptide of SEQ ID NO:6, GlyProGluIleLeuAspValProSerThr, whose inhibition of CS-1 binding is about equal to that of CS-1 itself, and is set at "one" in relative units. Jurkat cell binding inhibitions on the right are relative to each other, rather than to an external standard, with inhibition on the left and right caused by XLDFp being set equal to each other.

The present invention contemplates a cyclic inhibitor peptide, a composition containing such a peptide, and a process of using such a peptide. A contemplated cyclic peptide inhibits binding between the CS-1 peptide of fibronectin or sVCAM-1 and the inflammatory cell VLA-4 surface receptor, and is therefore often referred to herein as a cyclic inhibitor peptide.

Each of the cyclic peptides contemplated here can be viewed as a deletion analogue of a CS-1 or B12 peptide in that each is shorter in length; i.e., contains fewer residues. Each cyclic peptide inhibitor can also be considered a substitution analogue because of the presence of the Phe instead of Val adjacent the Asp residue, and the presence of two Xaa residues that together form a sulfur-containing chain or bridge and are not present in either CS-1 or B12. Additional substitutions and deletions from CS-1 and B12 peptides are also present in the contemplated inhibitors as is discussed hereinbelow.

A. Peptides

A contemplated cyclic peptide can be viewed as a mimic of the whole fibronectin molecule, or at least the 25-residue (25-mer) CS-1 portion of fibronectin (SEQ ID NO:5) that binds to the VLA-4 receptor. A contemplated cyclic peptide can also be viewed as a mimic for the VCAM-1 molecule or at least the region of that molecule that binds to VLA-4. A contemplated cyclic peptide will usually be discussed in regard to its CS-1-mimetic properties, but that is for the sake of convenience only. As will be seen from the discussion that follows, a contemplated peptide binds to the VLA-4 receptor even more tightly than does the CS-1 25-mer peptide present in fibronectin or the soluble form of VCAM-1, sVCAM-1.

Broadly, a contemplated cyclic inhibitor peptide can be defined as having a structure corresponding to formula I, below, R-Xaa$^1$-Z-Asp-Phe-Y-Xaa$^2$          I wherein R is (a) $R^1$ that is (i) absent so that the peptide is terminated by the free α-amine of Xaa or (ii) a $C_1$–$C_4$ acyl moiety, or (b) $R^2$ that is selected from the group consisting of phenylacetyl, benzoyl, phenylalanyl, tyrosyl, N-$C_1$–$C_4$ acyl phenylalanyl and N-$C_1$–$C_4$ acyl tyrosyl;

the $Xaa^1$ and $Xaa^2$ groups are α-amino acid residues that together form a sulfide or disulfide bond in a chain that contains 3 to about 6 atoms, including at least one sulfur atom between the α-carbons of the two Xaa groups, and in which $Xaa^2$ has a C-terminal carboxamide group, or the C-terminal carboxyl is replaced by hydrogen;

Z is absent, or a peptide selected from the group consisting of Pro-Glu-Leu, Phe-Leu, Glu-Phe-Leu, Pro-Glu-Phe-Leu (SEQ ID NO:2), and Gly-Pro-Glu-Phe-Leu (SEQ ID NO:3); and Y is absent, Pro, or $Y^1$ that is a peptide selected from the group consisting of Pro-Ser, Pro-Ser-Thr and Pro-Ser-Thr-Val (SEQ ID NO:4);

with the provisos that:

(i) R is $R^2$ when Z is absent, and (ii) $R^2$ is selected from the group consisting of phenylacetyl, benzoyl, N-$C_1$–$C_4$ acyl phenylalanyl and N-$C_1$–$C_4$ acyl tyrosyl when the two Xaa residues are separated by two amino acid residues.

Preferably, $Xaa^1$ and $Xaa^2$ form a disulfide bond and $Xaa^2$ has a carboxy-terminal carboxamide group so that a cyclic peptide of formula I reduces to a cyclic peptide of formula Ia, shown below,

R-Xaa-Z-Asp-Phe-Y-Xaa-NH$_2$      Ia wherein

R is (a) $R^1$ that is (i) absent so that the peptide is terminated by the free α-amine of Xaa or (ii) a $C_1$–$C_4$ acyl moiety, or (b) $R^2$ that is selected from the group consisting of phenylacetyl, phenylalanyl and N-$C_1$–$C_4$ acyl phenylalanyl;

at least one Xaa is an oxidized cysteine and the other Xaa is an oxidized cysteine, homocysteine or penicillamine residue such that the two Xaa's together form a disulfide bond;

Z is absent, or a peptide selected from the group consisting of Pro-Glu-Leu, Phe-Leu, Glu-Phe-Leu, Pro-Glu-Phe-Leu (SEQ ID NO:2), and Gly-Pro-Glu-Phe-Leu (SEQ ID NO:3); and Y is absent, Pro, or $Y^1$ that is a peptide selected from the group consisting of Pro-Ser, Pro-Ser-Thr and Pro-Ser-Thr-Val (SEQ ID NO:4);

with the provisos that:

(i) R is $R^2$ when Z is absent, and (ii) $R^2$ is phenylacetyl or N-$C_1$–$C_4$ acyl phenylalanyl when the two Xaa residues are separated by two amino acid residues; i.e., when both Z and Y are absent.

A cyclic peptide of formula I or Ia, as well as those of formulas II and III below, is water-soluble and inhibits the binding of Jurkat cells (ATCC TIB 152) to a solid phase-bound peptide of SEQ ID NO:5 in an in vitro assay in an aqueous buffer at a pH value of 7.2–7.4 to an extent that is about 5- to about 600-fold better (more potent) than the inhibition in said binding exhibited by a peptide of SEQ ID NO:3.

Examining formulas I and Ia, it is seen that only the Asp of the CS-1 (SEQ ID NO:5) and B12 (SEQ ID NO:9) fibronectin peptides is required to be present, as is a Phe residue that is not present in either CS-1 or B12. In addition to that two-residue sequence, the sequence/structure of a contemplated inhibitor peptide and the CS-1 or B12 portions can be similar, although a contemplated peptide here is cyclic, whereas the CS-1 and B12 peptides are linear. Still further, a most preferred cyclic inhibitor peptide is quite different in sequence from a CS-1 or B12 peptide.

In examining formulas I and Ia it is also seen that the N-terminal R group can be an $R^1$ group that is absent so that the N-terminus of a cyclic peptide is the free α-amine of the $xaa^1$ residue. R can also be an $R^1$ group that is a $C_1$–$C_4$ acyl moiety. Exemplary $C_1$–$C_4$ acyl moieties include formyl, acetyl (which is preferred), propionyl, n-butanoyl and iso-butanoyl.

As already noted, an R group can also be an $R^2$ group. An $R^2$ group is selected from the group consisting of phenylacetyl, phenylalanyl and N-$C_1$–$C_4$ acyl phenylalanyl.

As is noted in the above provisos, R is $R^2$ when Z is absent. In addition, when there are only two residues between the two Xaa residues of a cyclic peptide inhibitor, $R^2$ is further defined as being phenylacetyl or N-$C_1$–$C_4$ acyl phenylalanyl.

The above definition and provisos do not, of course, preclude R from being $R^2$ when Z is present, nor preclude $R^2$ from being phenylalanyl (Phe) when there are more than two residues between the two Xaa residues.

Z in an above formula can also be absent, in which case "R-$Xaa^1$" or "R-Xaa" is peptide-bonded directly to the depicted Asp residue. Z is absent in the most potent cyclic peptide inhibitor thus far examined, and that peptide and similar peptides can be considered to be further deletion analogues of CS-1 or B12.

In other embodiments, Z is a di-, tri-, tetra- or pentapeptide that is selected from the group consisting of Pro-Glu-Leu, Phe-Leu, Glu-Phe-Leu, Pro-Glu-Phe-Leu (SEQ ID NO:2), and Gly-Pro-Glu-Phe-Leu (SEQ ID NO:3). The di- through pentapeptide of a Z group is peptide bonded at both termini between "R-$Xaa^1$" or "R-Xaa" and the Asp residue.

When Z is present, the Z-Asp portion of a cyclic inhibitor peptide can be considered to be a substitution analog of the corresponding portion of a CS-1 or B12 peptide because the Ile residue present between the Glu and Leu residues of those VLA-4-binding peptides is replaced by a Phe residue here. That this Phe for Ile substitution is effective is surprising in view of the larger side chain of Phe as compared to Ile.

A Y group can also be absent from a cyclic inhibitor peptide, which is most preferred and also provides a further deletion from a CS-1 or B12 peptide. Y can also be a prolyl residue (Pro), which is preferred, or a di-, tri- or tetrapeptide that is selected from the group consisting of Pro-Ser, Pro-Ser-Thr and Pro-Ser-Thr-Val (SEQ ID NO:4) and is sometimes referred to herein as $Y^1$.

Thus, the Asp-Phe-Y- portion of a cyclic inhibitor peptide can be viewed as both a substitution analogue of a CS-1 and B12 peptide because of the substitution of Val with Phe, and a deletion analog of those peptides because of the relative shortness of a contemplated peptide compared to peptide CS-1 or B12. Valine (Val) is even of smaller size than Ile, so that successful substitution of the much larger Phe side chain for the smaller Val side chain was again unexpected.

Formulas I and Ia contain two Xaa residues or $Xaa^1$ and $Xaa^2$ groups that are α-amino acid residues that together form a sulfide or disulfide bond in a chain (bridge) that contains 3 to about 6 atoms, including at least one sulfur atom, between the α-carbons of the two Xaa groups. The group Xaa² has C-terminal carboxamide [—C(O)NH₂)] group or the C-terminal carboxyl is replaced by hydrogen.

Thus, the two Xaa groups each contain an α-carbon atom and there is a sulfur atom-containing chain or bridge of atoms between those α-carbon atoms. The sulfur-containing chain can contain one sulfur atom as where a sulfide bond is present in lanthionine, or can contain two sulfur atoms of a disulfide bond as in cystine.

Chains of varying lengths that contain a disulfide bond can be formed by the oxidation of mercaptan-containing residues such as cysteine, homocysteine or penicillamine. Chains of varying length that contain a sulfide bond can be formed by reaction of one of the above mercaptan-containing residues, with an appropriately blocked β-, γ- or K-leaving group-containing amino acid such as 2-N-t-Boc-amino-3-O-methanesulfonylpropionic acid, 2-N-succinimido-4-bromobutyric acid or 2-N-succinimido-5-iodipentanoic acid in a polar solvent in the presence of an excess of a non-nucleophilic base such as 4-dimethylaminopyridine or 1,8-bis(dimethylamino) naphthalene.

Preferably, a disulfide bond is present in the chain, and the Xaa groups are oxidized cysteine, homocysteine or penicillamine residues. More preferably, at least one Xaa is an oxidized cysteine (Cys) residue. The other Xaa residue is another oxidized cysteine, an oxidized homocysteine or oxidized penicillamine residue so that the two oxidized Xaa residues together form a disulfide bond. It is more preferred that both Xaa residues be oxidized Cys residues so that a cystine, disulfide-containing, residue is present.

A cyclic inhibitor peptide of formula I, and the other formulas herein, preferably contains a carboxy-terminal (C-terminal) carboxamide [—C(O)NH₂] group. However, a C-terminal carboxamide group of a cyclic inhibitor peptide can be replaced by hydrogen. When the C-terminal carboxamide group so replaced by hydrogen, Xaa² is not strictly speaking an "amino acid residue". However, such a Xaa² will be treated as an amino acid residue here for ease of discussion. Exemplary cyclic inhibitor peptides in which the C-terminal carboxamide group is replaced by hydrogen are illustrated in Table 1, hereinafter, below the entries for SEQ ID NO:33 and SEQ ID NO:19.

A contemplated cyclic inhibitor peptide inhibits the binding of inflammatory cells that contain the VLA-4 receptor [Jurkat cells (American Type Culture Collection, Rockville, Md. 20852, ATCC TIB 152)] to the solid phase-bound CS-1 peptide (SEQ ID NO:1) in an aqueous buffer at pH 7.2–7.4 to an extent that is about 5-fold to about 600-fold better than that binding exhibited by the standard 10-mer peptide of SEQ ID NO:6 [GPEILDVPST in single letter code]. More preferably that binding is inhibited by about 50- to about 600-fold, and most preferably by about 100- to about 600-fold better than that exhibited by the standard 10-mer.

Binding inhibition is measured here as a concentration of peptide that inhibits one-half the binding between a standard number of Jurkat cells and a standard amount of CS-1 peptide bound to the surface of a microtiter plate well. Those concentrations are conveniently expressed as IC₅₀ values, smaller numbers indicating a lower concentration required to inhibit 50 percent binding and therefore greater potency. Further specifics of this assay are provided hereinafter.

To recapitulate, a cyclic peptide of formula I inhibits binding between the CS-1 peptide region of fibronectin and the VLA-4 receptor. Those inhibitors that are about five-times better inhibitors than the standard 10-mer peptide of SEQ ID NO:6 are contemplated here, each of the cyclic peptides of formulas I, above, and II and III, below, is at least about five times more potent (better) than the standard 10-mer.

In more preferred practice, a cyclic peptide inhibitor contains two to five residues between the two Xaa residues in that such cyclic peptides exhibit a greater potency in inhibiting binding between VLA-4-expressing cells and the standard 10-mer peptide of SEQ ID NO:6. The reason for the noted enhanced potency is unknown, but may be due to a reduction in the rotational and/or vibrational degrees of freedom present in these molecules with fewer residues between the Xaa residues that tends to restrict the inhibitor peptide in a conformation that is relatively more favorable for binding inhibition. These more preferred molecules typically exhibit binding inhibition potencies that are about 50 to about 600 times that exhibited by a peptide of SEQ ID NO:6 in the standard in vitro assay.

Such a more preferred cyclic peptide corresponds to formula II, below,

wherein
R is
(a) R¹ that is (i) absent so that the peptide is terminated by the free α-amine of Xaa or (ii) a C₁–C₄ acyl moiety, or
(b) R² that is selected from the group consisting of phenylacetyl, phenylalanyl and N-C₁–C₄ acyl phenylalanyl;
at least one Xaa is an oxidized cysteine and the other Xaa is an oxidized cysteine, homocysteine or penicillamine residue such that the two Xaa's together form a disulfide bond;
Z¹ is absent or Phe-Leu; and
Y² is absent, Pro, Pro-Ser or Pro-Ser-Thr; with the provisos that:
(i) R is R² when Z¹ is absent, and
(ii) R² is phenylacetyl or N-C₁–C₄ acyl phenylalanyl when the two Xaa residues are separated by two amino acid residues.

As is seen above, R and Xaa are defined for a cyclic peptide of formula II as they were for an inhibitor peptide of formula Ia, as are the provisos the same. The Z and Y moieties are, however, more limited and are therefore defined as Z¹ and Y² in a cyclic peptide of formula II for greater clarity.

A still more preferred cyclic peptide corresponds in sequence to a peptide of formula III below

wherein
the two Cys residues are oxidized to form a cystine residue;
R¹ is a C₁–C₄ acyl moiety or absent so that the peptide is terminated by the free α-amine of the oxidized Cys residue; and
Y³ is Pro or Pro-Ser.

Thus, a still more preferred cyclic peptide inhibitor contains two oxidized Cys residues that form a cystine residue, as well as having a Z¹ Phe-Leu sequence between the N-terminal Cys and the Asp residue. These cyclic peptide inhibitors also include a Pro or Pro-Ser sequence as Y³ between the Phe and C-terminal Cys residues. These still more preferred cyclic peptide inhibitors exhibit a relative potency that is about 100 to about 300 times greater than that exhibited by the standard 10-mer peptide of SEQ ID NO:6 in the in vitro assay discussed before.

The presently most preferred and most potent peptide inhibitor is a single peptide corresponding to formula IV

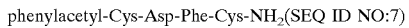

wherein the two Cys residues are oxidized form a disulfide-containing cystine residue. This most preferred cyclic inhibitor peptide is about 500–600 times more potent in inhibiting binding between the CS-1 peptide and Jurkat cells than is the standard 10-mer of SEQ ID NO:6.

Exemplary cyclic inhibitor peptides are listed in Table 1 below using single letter abbreviations along with their in vitro binding inhibition potencies toward Jurkat cells relative to the standard peptide of SEQ ID NO:6.

TABLE 1

Relative Potencies of Cyclic Peptide Inhibitors*

| SEQ ID NO: | Sequence | Relative Potency |
|---|---|---|
| 7 | φAcCDFC-NH$_2$[1] | 526 |
| 10 | CFLDFPC-N$_2$ | 253 |
| 11 | AcCFLDFPC-NH$_2$[2] | 134 |
| 12 | FCDFPC-NH$_2$ | 131 |
| 13 | CFLDFPSC-NH$_2$ | 122 |
| 14 | φAcJDFC-NH$_2$[1,3] | 94 |
| 15 | CFLDFPSTC-NH$_2$ | 81 |
| 16 | CPEFLDFPC-NH$_2$ | 56 |
| 17 | AcFCDFC-NH$_2$[2] | 52 |
| 18 | AcFCDFC-NH$_2$[2,5] | 41 |
| 33 | CPELDFPSC-NH$_2$ | 31 |
| — | φAcCDF-NHCH$_2$CH$_2$—[7] | 25 |
| 20 | CEFLDFPC-NH$_2$ | 19 |
| 21 | CFLDFPSTVC-NH$_2$ | 19 |
| 22 | CEFLDFPSTC-NH$_2$ | 9 |
| 23 | CGPEFLDFC-NH$_2$ | 9 |
| 24 | CEFLDFPSC-NH$_2$ | 6 |
| 19 | CPEFLDFPSC-NH$_2$ | 6 |
| — | φAcJDFc-NH$_2$[1,3,4] | 4 |
| 25 | FCDFC-NH$_2$ | 3 |
| 26 | ILDVPILDVP-NH$_2$[6] | 2 |
| 27 | ILDFP-NH$_2$[6] | 2 |
| 28 | CLDFC -NH$_2$ | 1 |
| 29 | AcFCDCP-NH$_2$[2] | 1 |
| 6 | GPEILDVPST | 1 |
| 30 | FCDCP-NH$_2$ | <1 |
| — | AcLDV-NH$_2$[6] | <1 |
| — | AcLDF-NH$_2$[6] | <1 |
| 31 | SFDFS-NH$_2$[6] | <1 |
| — | LDV-NH$_2$[6] | 0 |
| — | LDF-NH$_2$[6] | 0 |

*All peptides are cyclized via a disulfide bond unless otherwise indicated. Peptides having no depicted substituent on the N-terminal amino acid residue contain a free α-amino group.
[1] φAc = phenylacetyl.
[2] Ac = acetyl.
[3] J = penicillaminyl.
[4] c = D-Cys.
[5] Unoxidized, straight chain peptide.
[6] Straight chain peptide.
[7] The Cys mercaptyl sulfur atom is bonded to the free valence of the terminal methylene group to form a chain with a sulfide bond.

The data of Table 1 illustrate the before-discussed provisos and preferences in sequence. For example, those data for cyclic peptides of SEQ ID NO'S:10 and 20 show that two oxidized Cys residues are preferred over only one Cys and one other mercaptan-containing residue, although the exchange of one oxidized penicillaminyl residue for one oxidized Cys in the most preferred cyclic peptide inhibitor still provided an inhibitor that was about 100-times as potent as the standard, open chain 10-mer of SEQ ID NO:6.

The data for the peptides of SEQ ID NO'S:7, 17, 26 and 29 and compound φAcJDFC-NH$_2$ SEQ ID:14 illustrate the importance of R being an R$^2$ group when Z or Z$^1$ is absent. Those data and the remaining data illustrate that R can be either an R$^1$ or an R$^2$ group when Z or Z$^1$ are present.

The data for the peptides of SEQ ID NO's:7, 17, 23, 26, and 14 illustrate the importance of an R$^2$ group being phenylacetyl or N-C$_1$–C$_4$ acyl phenylalanyl for molecules in which the two Xaa residues are separated by two amino acid residues.

Table 1 still further illustrates the before-stated general preference for relatively shorter rather than longer sequences. Thus, all but one of the inhibitors that exhibited a relative potency of about 50 or greater contained a total of six or fewer residues. Contrarily, all but one of the peptide inhibitors that exhibited a relative potency of less than about 50 contained seven or more residues, or did not fulfill the requirements of a proviso, or did not contain a terminal carboxamide group.

The data of Table 1 also illustrate the unexpected enhancements in binding inhibition exhibited by an inhibitor peptide contemplated herein as compared to other peptides of the art. For example, the Leu-Asp-Val (LDV) peptide stated as being a minimal peptide required for binding of the VLA-4 receptor in WO 93/12809 exhibited a relative inhibitory binding activity of about 1 as the N-acetyl C-amide derivative and zero as the N-free amine C-amide as compared to the peptide of SEQ ID NO:3. Similar results were observed with Leu-Asp-Phe (LDF) that is not disclosed in that published application, but can be present in a cyclic peptide here.

Exemplary cyclic inhibitor peptides are also shown in Table 2 below as their chemical structure along with their in vitro binding inhibition potencies toward Jurkat cells relative to the standard peptide of SEQ ID NO:6.

TABLE 2

| Structure | Relative Potency |
|---|---|
| (chemical structure shown) | 1190 |

TABLE 2-continued

| Structure | Relative Potency |
|---|---|
| (structure) | 954 |
| (structure) | 901 |
| (structure) | 501 |
| (structure) | 358 |
| (structure) | 254 |

TABLE 2-continued

| Structure | Relative Potency |
|---|---|
| 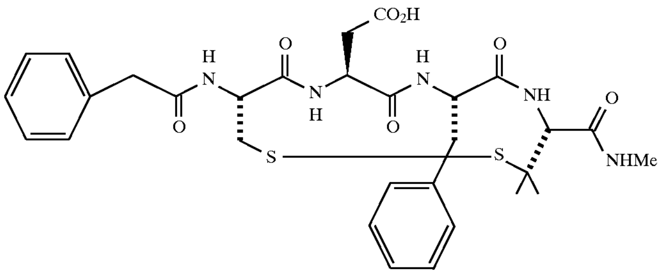 | 232 |
| 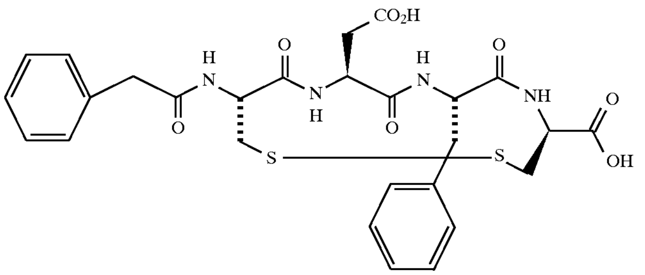 | 202 |
| 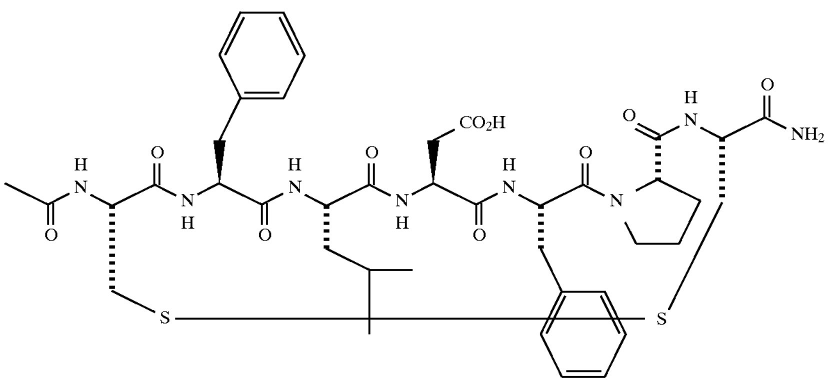 | 135 |
| 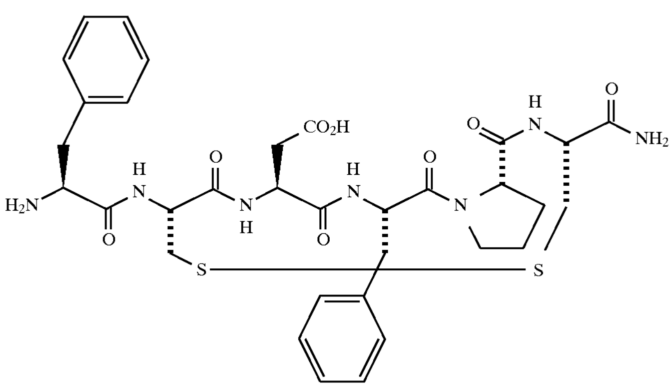 | 131 |

TABLE 2-continued

| Structure | Relative Potency |
|---|---|
| 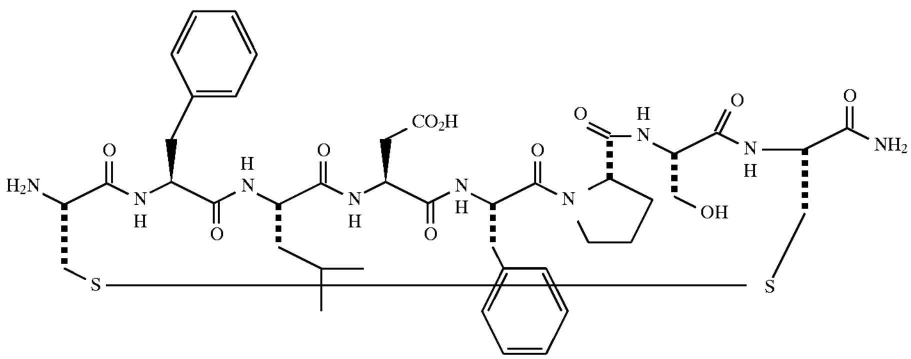 | 122 |
| 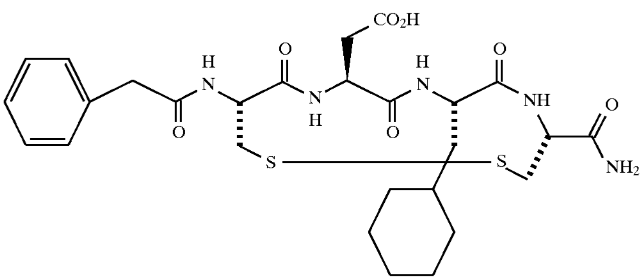 | 121 |
| 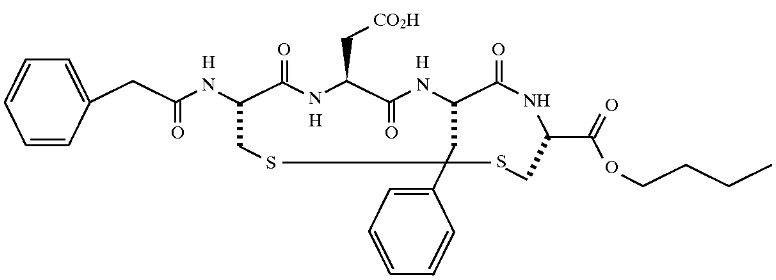 | 99.2 |
| 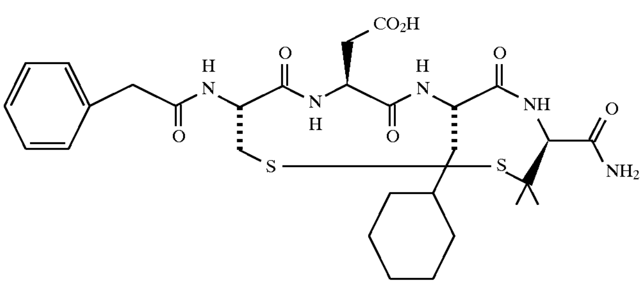 | 98.9 |
| 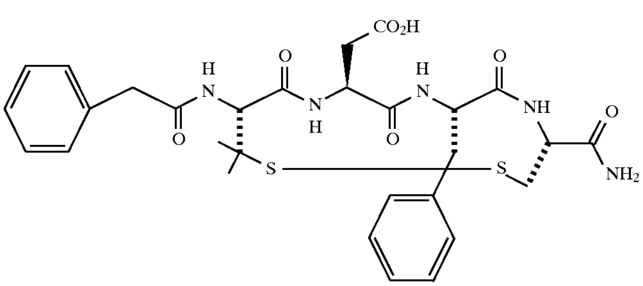 | 93.9 |

TABLE 2-continued

| Structure | Relative Potency |
| --- | --- |
| 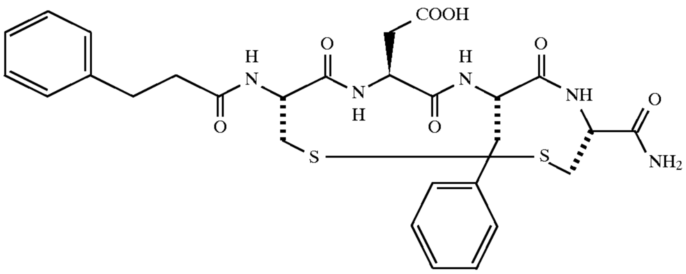 | 89.8 |
| 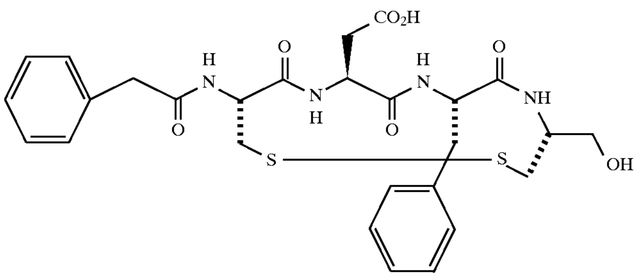 | 84.5 |
| 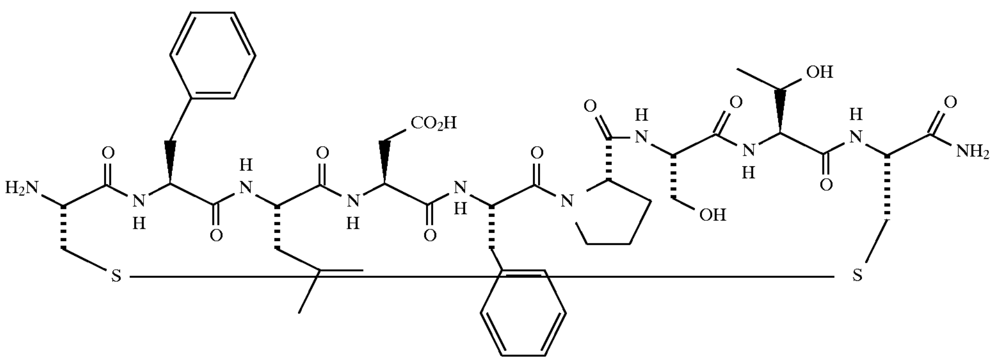 | 81.4 |
| 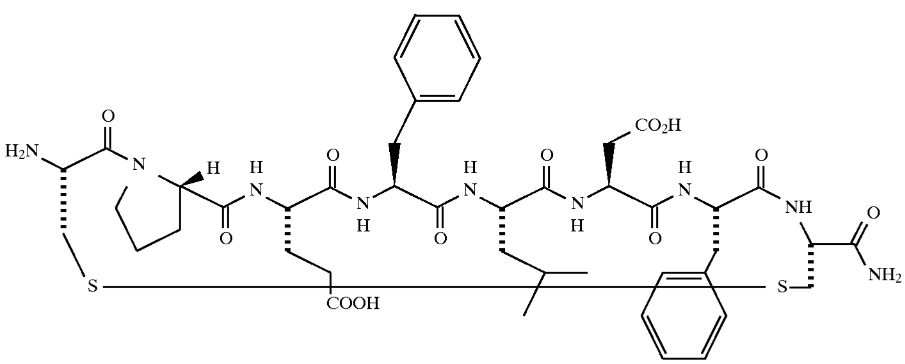 | 56.3 |

TABLE 2-continued

| Structure | Relative Potency |
|---|---|
| (structure) | 52.6 |
| (structure) | 46.6 |
| (structure) | 31.3 |
| (structure) | 30.7 |
| (structure) | 23.5 |

TABLE 2-continued

| Structure | Relative Potency |
|---|---|
| | 18.8 |
| | 18.8 |
| 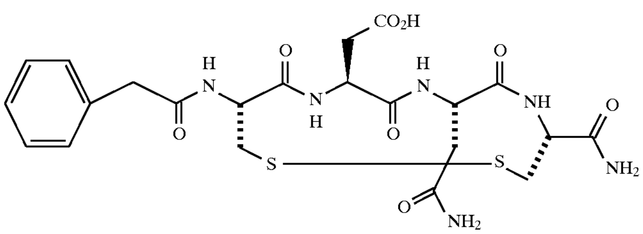 | 18.2 |
| 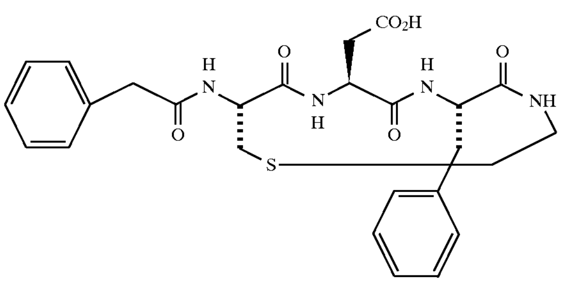 | 16.1 |
| 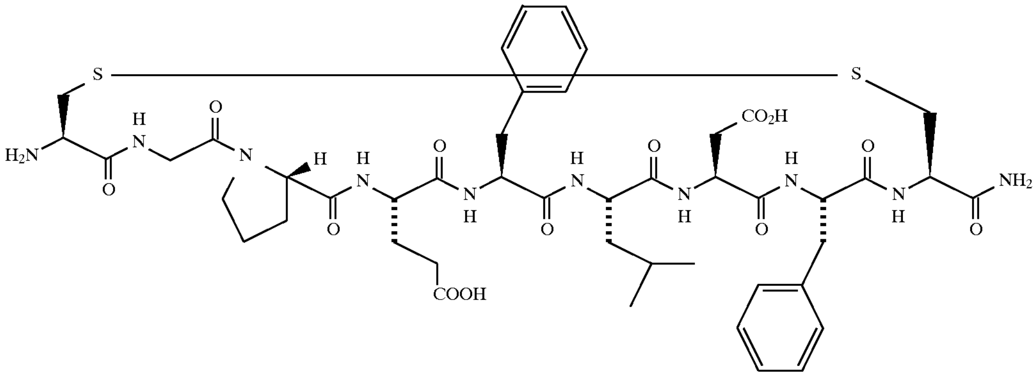 | 9.39 |

TABLE 2-continued

| Structure | Relative Potency |
|---|---|
| 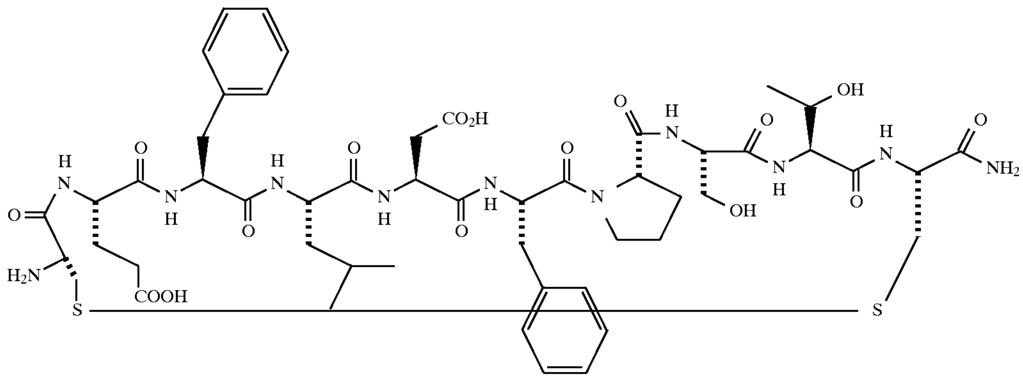 | 9.39 |
| 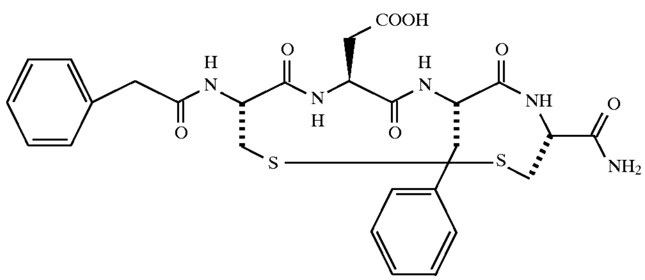 | 7.2 |
| | 6.26 |
| | 6.26 |

TABLE 2-continued

| Structure | Relative Potency |
|---|---|
| 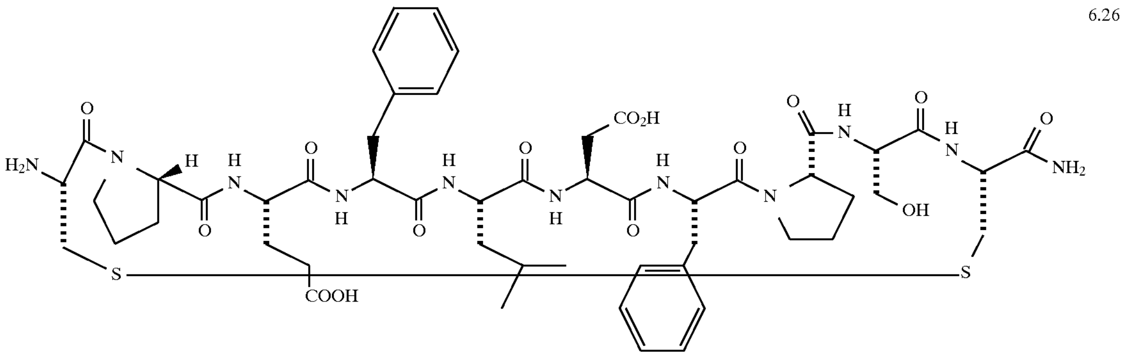 | 6.26 |
| 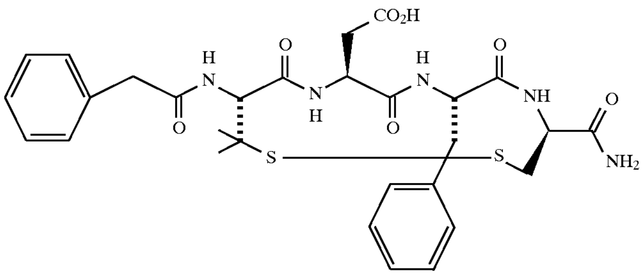 | 4.7 |
| 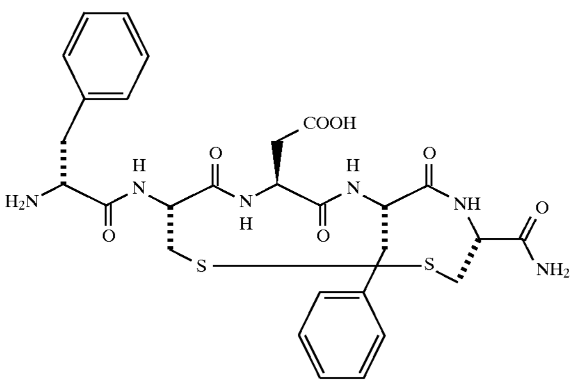 | 3.13 |
| 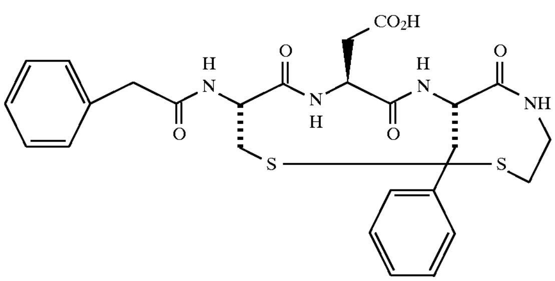 | 2.92 |

TABLE 2-continued

| Structure | Relative Potency |
|---|---|
| [structure] | 2.52 |
| [structure] (SEQ ID NO:32) | .91 |
| [structure] | 0 |
| [structure] | 0 |
| [structure] | 0 |

A preferred cyclic inhibitor peptide has the following formula:

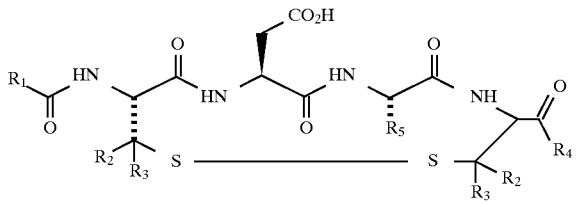

where $R_1$ is a phenyl or pyridyl group connected by a lower alkyl. $R_2$ is a H or methyl group. $R_3$ is a H or methyl group. $R_4$ is a amine (—$NH_2$), lower alkyl amine, lower alkyl ester or hydroxyl group. $R_5$ is a phenyl, pyridyl or cyclohexane group connected by a lower alkyl. A lower alkyl is one to five carbon atoms long.

In addition to being more potent than the CS-1 or standard 10-mer peptides, a contemplated cyclic inhibitor peptide is relatively more stable in serum that is the CS-1 peptide. Thus, the cyclic inhibitor peptide at SEQ ID NO:7 exhibited no loss of potency after 24 hours in PBS at 7.2–7.4 that also contained 10 percent mouse or human serum. Contrarily, the CS-1 peptide lost its potency in less than one hour under the same conditions.

The straight chain polypeptides disclosed in jointly assigned, co-pending application Ser. No. 08/164,101, filed Dec. 6, 1993, now abandoned, were also assayed for their inhibition of CS-1 binding to VLA-4 and were found to be superior to CS-1 or the 10-mer standard used herein. When those peptides were assayed for the inhibition of binding of VLA-4 to recombinant, soluble VCAM-1 (sVCAM-1), their relative binding inhibition was about the same to worse when compared their CS-1 inhibitions, as is shown in FIG. 1.

Binding inhibition studies carried out using a herein contemplated cyclic inhibitor peptide such as previously discussed most preferred compound, showed an unexpected reversal of relative binding potencies. Thus, the best straight chain peptide of application Ser. No. 08/164,101, filed Dec. 6, 1993, now abandoned, having the sequence φAcLeuAspPhe-morpholinamide (XLDFZ) inhibited binding by CS-1 about 844-times more potently than did the Standard 10-mer of SEQ ID NO:6. Relative to the Standard 10-mer, the inhibition potencies of that XLDFZ peptide, the XLDFp and the most preferred cyclic peptide of SEQ ID NO:7 were about 844:313:563, respectively. Relative to each other, those ratios become about 2.7:1:1.8. When compared against each other for inhibiting Jurkat cell binding to solid phase-bound sVCAM-1, the relative potencies were about 1.3:1:3.8, respectively. Thus, the illustrative cyclic peptide exhibited about two-thirds the potency of the best linear peptide for inhibiting Jurkat cell binding to CS-1, and about 3 times the potency of that same linear peptide when used as an inhibitor of Jurkat cell binding to sVACM-1.

Interestingly, peptides of the formulas φAc-LeuAspSer-D-Pro- (XLDSP) and SEQ ID NO:6 that exhibited relative binding inhibitions between Jurkat cells and solid phase-bound CS-1 of about 17 and 1, respectively, exhibited no inhibition of binding between solid phase-bound sVCAM-1 and Jurkat cells. Similarly, neither the cyclic peptide of SEQ ID NO:10 nor the cyclic φAcCDF-$NHCH_2CH_2$- peptide that were excellent inhibitors of binding to CS-1, exhibited inhibition of Jurkat cells binding to sVCAM-1.

A sVCAM-1/VLA-4 inhibition thus appears to have somewhat different, and unpredictable requirements from inhibition of binding to CS-1 to VLA-4.

B. Syntheses

The contemplated inhibitors are peptides or peptide derivatives, and as such, can be readily synthesized using well known synthetic methods. Specific synthetic examples are provided hereinafter.

Standard solid phase synthesis was used here. Thus, the N-protected, C-terminal residue was linked to a solid support having a benzhydrylamine substituent. Fmoc amine blocking groups were used in these syntheses, although t-Boc, CBZ or other blocking groups can also be used with other solid supports. Upon deblocking the Fmoc group with piperidine, another residue was coupled. That coupling was followed by further deblocking, coupling, deblocking etc. steps until a solid phase-linked peptide of desired sequence was prepared. As appropriate to each peptide, an N-terminal R group was added after a final N-deblocking step. The desired peptide and any accompanying functional group protecting groups were removed from the solid support by reaction with trifluoroacetic acid (TFA). This procedure results in a C-amide-terminated peptide when a benzhydrylamine solid support is used.

Contemplated peptides can also be prepared using t-Boc N-protecting groups and another solid support, or a benzylamino-substituted solid support to which a p-hydroxymethylphenylcarboxyl (PAM) group is first reacted with the amine of the support to form a carboxamide. The hydroxyl group is then used to form an ester link to the first peptide and standard t-Boc synthetic technology is thereafter followed. Reaction of the completed, deprotected solid phase-linked peptide with ammonia provides the C-terminal amide peptide.

In other embodiments, liquid phase peptide syntheses can be utilized. For example, a C-amido N-free amino group-containing amino acid derivative is coupled in solution to the carboxyl of a t-Boc-protected residue using a carbodiimide. The t-Boc protecting group is removed from the resulting dipeptide with acid, a further t-Boc-protected residue is similarly added, followed by similar deblockings and further additions. The N-terminal R group such as phenylacetic acid is added after the last t-Boc removal step and the synthesis is completed, except for deprotecting the Asp residue. That step is carried out by catalytic hydrogenation where a benzyl ester protecting group was used.

The cyclization can be carried out in one of two ways; either by the oxidation of the fully deprotected thiol-containing peptide, using oxygen, potassium ferricyanide, or other oxidant (Introduction to Cleavage Techniques, published by Applied Biosystems, 1990), or by the iodine oxidation of the peptide in which the thiol groups are protected with a benzyl, acetamidomethyl, or other similar protecting group [Kamber et al., *Helv. Chim. Acta*, 63(4):899–915 (1980)]. In the latter case, the protecting groups are removed during the course of the reaction.

Regardless of the synthetic method used, an inhibitor peptide is typically recovered and purified prior to use. Recovery and purification techniques are well known and will not be dealt with here.

C. Compositions and Processes

As noted elsewhere, immune system leukocyte effector or inflammatory cells such as monocytes, T cells and eosinophils bear the VLA-4 receptor on their cell surfaces. Those cells bind to the CS-1 portion of fibronectin present on the surfaces of vascular endothelial cells at an early step in inflammatory cell emigration (trafficking) from the blood in the tissues. These inflammatory cells immunoreact with monoclonal antibody P4C2 discussed in Wayner et al., *J. Cell. Biol.*, 109:1321–1330 (1989), Wayner WO 98/12809, Hemler et al, *J. Biol. Chem.*, 262(24):11478–11485 (1987)

and monoclonal antibody HP1/2 of Lobb WO 93/13798 published Jul. 22, 1993.

Once in the tissues, the inflammatory cells enhance the inflammatory response through one or more of several mechanisms. In one mechanism, cytokines and chemoattractants such as interleukin-1β (IL-1β), IL-2, tumor necrosis factor α (TNFα) and lymphocyte-derived chemotactic factor are released by the inflammatory cells and cause further inflammatory cells to emigrate to the area. In another mechanism, the inflammatory cells mis-recognize cells of the mammal with the inflammatory disease state as being non-self and attack those cells, killing them. These and other mechanisms of immunoinflammatory response enhancement are well known to skilled workers and need not be further elaborated upon here. The fibronectin CS-1 peptide thus mediates inflammatory disease states by assisting emigration of inflammation-enhancing effector cells from the blood into the tissues.

A before-discussed cyclic inhibitor peptide blocks binding between CS-1 and VLA-4, and inhibits the resulting emigration of inflammatory cells bearing VLA-4 receptors into the tissues, and the exacerbation of the inflammatory condition that results. That inhibition of emigration of inflammatory cells results in a reduction of the fibronectin CS-1/VLA-4-mediated inflammatory response caused by those inflammatory cells, and thereby reduces the observed inflammation.

Particular inflammatory disease states that are mediated by CS-1 and VLA-4, and in which a contemplated inhibitor peptide can diminish inflammation are quite broad. Illustrative of those types of inflammation are asthma, arthritic conditions such as rheumatoid arthritis and osteoarthritis, allograft rejection, various types of skin inflammation, and demyelinating diseases of the central nervous system.

Specific pathological inflammatory conditions in which expression of CS-1 has been found to be implicated and where no such expression is observed in absence of a pathological condition (i.e., in normal tissue) include: rheumatoid arthritis (synovium), osteoarthritis (synovium), skin psoriasis, kidney transplant, asthmatic lung, and lymph node high endothelial venules (HEV) in humans, as well as in the gut of monkeys infected with SIV and those having inflammatory bowel disease, rabbits having asthmatic lungs and heart transplants, mouse brain in experimental autoimmune encephalomyelitis (EAE) and skin in delayed type hypersensitivity (DTH), and the joints of rats with induced arthritis.

A pharmaceutical composition containing a before-discussed cyclic inhibitor peptide such as a peptide of formula I dissolved or dispersed in a pharmaceutically acceptable carrier or diluent that is preferably aqueous is also contemplated for use in treating a CS-1/VLA-4-mediated inflammatory disease state such as those discussed before. Such a composition contains a CS-1/VLA-4 binding-inhibiting (an inflammation-reducing) amount of a before-discussed, contemplated cyclic inhibitor peptide.

Thus, the present invention also contemplates a pharmaceutical composition that can be used in treating the aforementioned conditions. A contemplated pharmaceutical composition is comprised of a before-described cyclic inhibitor peptide such as a cyclic peptide of formula I that inhibits the binding interaction between VLA-4-containing leukocytes and the fibronectin peptide CS1 portion expressed on endothelial cell surfaces, which peptide is dissolved or dispersed in a pharmaceutically acceptable diluent in a binding inhibitory (inflammation-reducing) amount. A contemplated pharmaceutical composition is suitable for use in a variety of drug delivery systems. For a brief review of present methods for drug delivery, see, Langer, *Science*, 249:1527–1533 (1990).

For a contemplated pharmaceutical composition, the dose of the cyclic peptide varies according to, e.g., the particular peptide, the manner of administration, the particular disease being treated and its severity, the overall health and condition of the patient, and the judgment of the prescribing physician or veterinarian. A pharmaceutical composition is intended for parenteral, topical, oral or local administration, such as by aerosol or transdermally, for prophylactic and/or therapeutic treatment. A pharmaceutical composition can be administered in a variety of unit dosage forms depending upon the method of administration. For example, unit dosage forms suitable for oral administration include powder, tablets, pills, capsules and dragees.

Preferably, in one embodiment, a pharmaceutical composition is administered parenterally such as intravenously, subcutaneously, intramuscularly or interperitoneally. Thus, a composition for intravenous administration is particularly contemplated that comprises a solution of a contemplated inhibitor peptide dissolved or dispersed in a pharmaceutically acceptable diluent (carrier), preferably an aqueous carrier. A variety of aqueous carriers can be used, e.g., water, buffered water, 0.9 percent saline, buffered aqueous ethanol solutions and the like. These compositions can be sterilized by conventional, well known sterilization techniques, or can be sterile filtered. The resulting aqueous solutions can be packaged for use as is, or lyophilized, the lyophilized preparation being combined with a sterile aqueous solution prior to administration. A composition can contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

The concentration of cyclic inhibitor peptide utilized is usually at or at least about 0.0001 percent to as much as about 0.1 percent by weight and is selected primarily by fluid volumes, viscosities, etc., in accordance with the particular mode of administration selected.

Thus, a typical pharmaceutical composition for intravenous infusion can be made up to contain 250 ml of sterile Ringer's solution normal saline or PBS, and up to about 2.5 mg of a cyclic inhibitor peptide. Actual methods for preparing parenterally administrable compounds are known or apparent to those skilled in the art and are described in more detail in for example, *Remington's Pharmaceutical Sciences*, 17th ed., Mack Publishing Company, Easton, Pa. (1985), which is incorporated herein by reference.

For solid compositions, conventional nontoxic solid diluents (carriers) can be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10–95 percent of active ingredient, that is, a before-described inhibitor peptide preferably about 20 percent (see, *Remington's*, supra), preferably using an enteric coating to pass a solid dose through the stomach and into the intestine.

For aerosol administration, another preferred embodiment, a contemplated cyclic inhibitor peptide is preferably supplied as a pharmaceutical composition in solution such as aqueous ethanol or DMSO solution along with a surfactant and propellant. Typical percentages of a cyclic inhibitor peptide are about 0.0001 percent to about 0.1 percent by weight, and preferably about 0.0001 percent to about 0.001 percent. The surfactant must of course, be nontoxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride such as, for example, ethylene glycol, glycerol, erythritol, arabitol, mannitol, sorbitol, the hexitol anhydrides derived from sorbitol, and the polyoxyethylene and polyoxypropylene derivatives of these esters. Mixed esters, such as mixed or natural glycerides can be employed. The surfactant can constitute about 0.1 to about 20 percent by weight of the composition, and preferably about 0.25 to about 5 percent. The balance of the composition is ordinarily propellant. Liquefied propellants are typically gases at ambient conditions, and are condensed under pressure. Among suitable liquefied propellants are the lower alkanes containing up to 5 carbons, such as butane and propane; and preferably fluorinated or fluorochlorinated alkanes. Mixtures of the above can also be employed. In producing the aerosol, a container equipped with a suitable valve is filled with the appropriate propellant, containing the finely divided compounds and surfactant. The ingredients are thus maintained at an elevated pressure until released by action of the valve. A pump-activated spray using air as propellant (atomizer or nebulizer) is also contemplated.

For example, for the treatment of asthma in rabbits, the dose of a contemplated cyclic peptide is in the range of about 1 to 100 mg/day for a 2–3 kg animal. For a human asthma patient, that dose is in the range of about 1 to about 100 mg/day for a 70 kg patient. Administration for asthma is typically by aerosol from a nebulizer. Ideally, therapeutic administration should begin as soon as possible after the attack begins.

A pharmaceutical composition containing a cyclic inhibitor peptide can be administered for prophylactic and/or therapeutic treatments. In therapeutic applications, a composition is administered to a patient already suffering from a disease, as described above, in an amount sufficient to inhibit binding between VLA-4-expressing leukocytes and endothelial cells that express the CS-1 peptide portion; i.e., reduce inflammation and thereby at least partially arrest the symptoms of the disease and its complications. An amount adequate to accomplish this is referred to as "therapeutically effective dose", or a "binding-inhibiting amount", or an "inflammation-reducing amount", or a "CS-1/VLA-4-inhibiting amount", or by a similar phrase. Amounts effective for this use depend on the severity of the disease and the weight and general state of the patient, but generally range from about 1 mg/kg to about 500 mg/kg of cyclic inhibitor peptide per day, with dosages of from about 1 mg/kg to about 10 mg/kg of a compound per day being more commonly used.

In prophylactic applications, a composition containing a contemplated peptide is administered to a patient susceptible to or otherwise at risk of a particular disease. Such an amount is defined to be a "prophylactically effective dose" and is also an amount sufficient to inhibit binding of VLA-4-expressing leukocytes to CS-1 peptide-expressing endothelial cells. In this use, the precise amounts again depend on the patient's state of health and weight, but generally range from about 1 mg/kg/day to about 500 mg/kg/day, more commonly from about 1 mg/kg/day to about 20 mg/kg/day.

Another way to assess a binding-inhibiting amount of a contemplated cyclic inhibitor peptide is to compare binding inhibition exhibited by the cyclic peptide to that provided by CS-1 or the 10-mer standard in an in vitro study. One convenient way to make that comparison is by use of $IC_{50}$ values of the two compared materials, and base the amount used on the amount of CS-1 or standard 10-mer peptide and an amount of the cyclic inhibitor peptide that is a multiple of the $IC_{50}$ value for that reference compound.

Typically, a compound whose $IC_{50}$ value is at least about one-fifth that of the standard 10-mer (five-times more potent), when used at one-fifth the molar amount of the 10-mer standard is a useful binding-inhibiting amount. More preferably, the amount is about one-fiftieth the amount of the 10-mer. More preferably still, the amount is equal to about one-hundredth that of the 10-mer. Inasmuch as those amounts inhibit binding by about 50 percent, greater concentrations that inhibit binding still further are preferred.

Thus, for in vitro use, a minimal CS-1/VLA-4-inhibiting amount is the $IC_{50}$ value. For in vivo use, the CS-1/VLA-4-inhibiting amount usually used begins with the $IC_{50}$ value concentration, and can decrease as required or one can increase to the solubility limit of the cyclic peptide in the utilized aqueous medium; i.e., the aqueous medium at pH 7.2–7.4 used such as normal saline where parenteral administration is used or intestinal fluid where oral administration is used.

Single or multiple administrations of a composition can be carried out with dose levels and pattern being selected by the treating physician or veterinarian. In any event, a pharmaceutical composition is formulated to provide a quantity of a cyclic inhibitor peptide sufficient to effectively treat the patient.

A process for treating fibronectin CS-1/VLA-4-mediated inflammation is also contemplated. In accordance with such a process, a before-described, contemplated cyclic inhibitor peptide is administered to a mammal in need of such a treatment such as a mammal having such inflammation or prophylactically as prior to an allograft. This administration is preferably via a before-discussed pharmaceutical composition. The cyclic peptide is administered in an inflammation-reducing (CS1/VLA-4-inhibiting) amount. The mammal such as mouse, rat, rabbit, monkey or human is maintained until the peptide is eliminated by a natural bodily process such as degradation and excretion. Multiple administrations in a single day, over a period of days or weeks, or for the life of the host mammal, where the mammal is the recipient of an allograft, are contemplated, as are single administrations.

Methods for determining an amount sufficient to inhibit binding between CS-1 and VLA-4 have already been discussed, particularly for in vitro studies. For in vivo uses, there are many published assays to determine if inflammation has been reduced by a particular treatment. For example, one can assess the number of painful joints in an arthritic patient or the patient's mobility before and after treatment. Reduction of effects of an asthma attack can be assayed by measurement of dynamic compliance or lung resistance in laboratory animals as is also well known. The amount of edema observed in DTH is also readily measurable, as are the effects of allograft rejection or its absence compared to standard controls.

BEST MODE FOR CARRYING OUT THE INVENTION

EXAMPLE 1
Exemplary Solid Phase Peptide Syntheses

Fmoc protected amino acids, hydroxybenzotriazole (HOBt) and Rink amide MBHA resin were obtained from Nova Biochem, La Jolla, Calif. Diisopropylcarbodiimide (DIC) was obtained from Chem Impex Inc., Chicago, Ill. Piperidine was obtained from Aldrich Chemical Company, St. Louis, Mo. Dimethylformamide (DMF), isopropanol (IPA), dichloromethane (DCM), and dimethylacetamide (DMA) were obtained from Burdick and Jackson, Muskegon, Mich. All of the above reagents were used as supplied by the manufacturer, with no further purification.

The standard deprotection/coupling cycle iterated during this synthesis is described in terms of the first coupling of Fmoc-Cys(Trt) to the Rink amide MBHA resin: The loading of the starting resin was 0.5–0.7 mmol/g polystyrene, and 0.1 or 0.25 meq were used in each synthesis. A typical reaction cycle proceeded as follows: (1) the N-terminal Fmoc group was removed with 25 percent piperidine in dimethylformamide (DMF) for 5 minutes, followed by another treatment with 25 percent piperidine in DMF for 15 minutes. The resin was washed five times with DMF. An N-methylpyrolidone (NMP) solution of a 4 to 10 fold excess of a pre-formed 1-hydroxybenzotriazole ester of the appropriate Fmoc-amino acid [Fmoc-Cys(Trt)] was added to the resin and the mixture was allowed to react for 30–90 minutes. The resin was washed with DMF in preparation for the next elongation cycle.

EXAMPLE 2
In Vitro Binding Assays

Jurkat cells (ATCC TIB 152), a human T lymphoblastic line, labeled with $^{51}$chromium were used to assay in vitro binding inhibition provided by various peptides discussed herein. COSTAR™ 96 well flat-bottom microtiter plates (catalog No. 9050, Cambridge, Mass.) were found to provide the best results in these assays.

The plates were prepared as follows: The 25-mer CS-1 peptide (SEQ ID NO:5) dissolved at 0.5–1 µg/ml in a buffer of 0.1M NaHCO$_3$ at pH 9.5 that also contained 10 µg/ml of bovine serum albumin (BSA) or a conjugate of the CS-1 peptide linked to ovalbumin (CS-1-OVA) dissolved at 1–2.5 µg/ml in the same buffer was used as the substrate. Each well of the microtiter plates was coated with 50 µl of substrate or buffer alone for controls. The wells were permitted to dry out completely and were then rinsed twice with PBS at pH 7.4. Non-specific binding sites of each well were then blocked using 200 µl per well of RPMI/1 percent BSA for two hours at room temperature. Both solid phase-affixed substrates provided similar results.

Jurkat cells (3–5×10$^6$ cells) were placed into a 15 ml FALCON™ round-bottom tube with a cap. The tube was centrifuged, and the extra medium was then removed.

Two hundred microliters of a $^{51}$Cr labeling solution were added to the centrifuged cells and maintained in contact with the cells for 90–120 minutes in a warm room. This procedure typically provides about 50,000–100,000 cpm/well with about 80–100 percent cell viability. Longer contact times provide a greater amount of labeling but lower cell viability.

The labeled cells were washed with (i) complete medium, (ii) 1mM EDTA/PBS and then (iii) RPM1/1 percent BSA free of serum components. The cells were centrifuged after each washing. The cells were finally resuspended in serum-free RPMI/1 percent BSA at a concentration of 1×10$^6$ viable cells/ml, which provides a concentration that is diluted by one-half in the assay.

Cyclic inhibitor peptides were prepared as stock solutions at 20 mg/ml in DMSO in 1.5 ml cryogenic screwcap vials, and were stored at −70° C. Using FLOW™ round-bottom or V-bottom microtiter plates, the inhibitor peptides were prepared at twice the assay concentration in RPMI/1 percent BSA at 60 µl/well.

Four initial dilutions were typically used. For less potent peptides such as the standard 10-mer of SEQ ID NO:6, the initial dilutions were 500 µg/ml, 100 µg/ml, 20 µg/ml and 4 µg/ml. For more potent peptides such as the peptide of SEQ ID NO:10, the typical initial concentrations were 10 µg/ml, 2 µg/ml, 0.4 µg/ml and 0.08 µg/ml.

The $^{51}$Cr-labeled cells (1×10$^6$ cells at 60 µl/well) were then admixed with the diluted cyclic peptide solutions. The admixtures were maintained at room temperature (about 22° C.) for 30 minutes.

One hundred microliters of each inhibitor peptide/cell admixture were transferred to the substrate-coated wells. This was done in triplicate for each dilution. The resulting plates were incubated for 30 minutes at 37° C. and then washed gently three times with RPMI/1 percent BSA at 200 µl/well. Binding was observed microscopically, particularly after the second wash.

The bound cells were then lysed by the addition of a 0.5 percent solution of sodium dodecylsulfate in water at 100 µl/well. The resulting solutions were then processed for counting and calculation of IC$_{50}$ values following usual procedures. Appropriate positive and negative controls were used with each plate so that the results of separate assays could be normalized and compared.

The potency data of Table 1 and Table 2 are so normalized. The absolute IC$_{50}$ value for the peptide of SEQ ID NO:7 is 0.3 µM.

Assays conducted using sVCAM-1 as solid phase-bound antigen were carried out substantially identically to those using CS-1. The sVCAM-1 polypeptide used had the same amino acid residue sequence as the materials described in Lobb et al., *Biochem. Biophys. Res. Commun.*, 178:1498–1504 (1991) and Cybulsky et al., *Proc. Natl. Acad. Sci., USA*, 88:7859–7863 (1991). Human embryonal kidney line 293 (ATCC CRL 1573) cells were co-transfected with a plasmid (pCDNAI;invitrogen) containing the sVCAM-1 DNA sequence and plasmid pSV2-neo [Southern et al., *J. Mol. Appl. Gen.*, 1:327–341 (1992)]. Cells were selected in DMEM, 10 percent fetal bovine serum and 600 µg/ml Geneticin. sVCAM-1 was purified from supernatants using a column containing monoclonal antibody P3H12 (anti-human VCAM-1) coupled to Sepharose 4B. The sVCAM-1 was eluted using 0.1M glycine at pH 2.5 following 50 column washes with PBS, pH 7.2. The eluate was immediately neutralized and dialyzed against PBS for use.

EXAMPLE 3
Delayed Type Hypersensitivity in Mice

An adoptive transfer delayed-type hypersensitivity murine model has been developed using splenic T cells primed to oxazolone. This model is described in Elices et al., *Clin. Exp. Rheum.*, 11(*Suppl.* 8):577–580 (1993), whose procedures are followed here.

Thus, BALB/c mice are shaved on the belly and painted (50 µl on the belly and 5 µl on each paw) with three percent oxazolone in acetone/olive oil (4:1) at days zero and 1. At day 5, the mice are sacrificed, their spleens removed, and splenic T cells are obtained via nylon wool columns.

Normal saline or saline containing 25×10$^6$/animal of the oxazolone-immune T cells are separately injected into naive mice. The mice are then challenged by painting 10 µl of 2 percent oxazolone onto one ear each. All procedures are carried out under sterile conditions and in endotoxin-free buffers.

Prior to challenge or saline injection, the mice are implanted with pumps that subcutaneously administered normal saline, normal saline containing a cyclic inhibitor peptide such as the cyclic peptide of SEQ ID NO:10 or normal saline containing a control peptide continually at 6 mg/kg/day for a 24-hour time period. The swelling diameter at the site of challenge or saline injection is measured with a microcaliper 24 hours thereafter.

The results of this study show that administration of a contemplated inhibitor peptide reduces this type of CS1/VLA-4-mediated immunoinflammation as compared to the untreated controls. Use of the control peptide provides no reduction of inflammation.

EXAMPLE 4
Treatment of Asthmatic Rabbits

Six New Zealand white rabbits are immunized with house dust mite antigen from birth through four months of age. Upon immunization, three rabbits receive a single nebulizer administration of a cyclic inhibitor peptide such as the cyclic peptide of SEQ ID NO:4 in aqueous 50 percent ethanol as diluent in an amount of 100 mg/kg, and the other three receive diluent alone. All of the rabbits are challenged with house dust mite antigen about 15–30 minutes after administration of the peptide, with those animals not receiving cyclic inhibitor peptide serving as controls.

Once immunized and challenged, the inflammatory state subsides to a basal level within about three weeks. The three animals used as controls are thereafter used as subjects for receipt of an inhibitor peptide, and the three rabbits that initially received the peptide serve as controls.

Using such a crossover study, the three initial control rabbits are treated with the above cyclic inhibitor peptide in the above diluent at a time more than three weeks after the above study, and the three previous recipients of the cyclic peptide are administered the diluent alone. All six are then challenged again.

Initial pulmonary function, measured by dynamic compliance ($C_{dyn}$) and lung resistance ($R_L$) and bronchoalveolar lavage (BAL) to obtain an effector cell count, here eosinophils, are conducted prior to administration of the cyclic peptide or diluent for both portions of this crossover study. Similar assays are then taken one-half hourly after challenge for six hours (early phase allergic reaction) and at 24 hours after challenge (late stage allergic reaction) for both portions of this study.

These studies are conducted as described by W. J. Metzger in *CRC Handbook of Late Phase Reactions*, W. Dorsch, ed., Chapter 35, CRC Press, Boca Raton, Fla. (1990) pages 347–362.

The results of this study for the pulmonary function parameters show the $C_{dyn}$ value for the challenged and treated animals stay at about the initial value for the whole six hours. The $C_{dyn}$ for the challenged, untreated animals quickly falls from the initial value and then stays at about that value for the whole six hours.

The $R_L$ values for the challenged, inhibitor peptide-treated animals remains between the initial value and a somewhat elevated value for the whole six hours. The $R_L$ values for the challenged, but untreated animals rises to several times the above elevated value for the last four hours.

The BAL count from these studies indicates a reduction in eosinophils after 24 hours in the inhibitor peptide-treated, challenged animals as compared to the untreated, challenged animals in the crossover study.

EXAMPLE 5
Rabbit Cardiac Allograft Model

New Zealand white rabbit SPF hearts are allografted into the necks of similar rabbits to assay a graft-vs-host immunorejection model and the effect of a contemplated peptide on that immunoinflammatory response.

Here, seven rabbits are injected on day zero with 1 mg/kg/day of the inhibitor peptide such as the cyclic peptide of SEQ ID NO:7 in aqueous diluent. The two rabbits then each receive a grafted heart, with the graft being made in the carotid artery to the aorta of the grafted heart, and the jugular vein to the pulmonary artery of the grafted heart. The rabbits thereafter receive daily injections of the same dose of that peptide, and are sacrificed on day 7. Another seven animals receive normal saline injections in place of the peptide injections, also receive a similarly allografted heart, and are similarly sacrificed at day 7.

The animals' blood vessels are thereafter examined histologically for evidence of arteriopathy, and particularly thickening of the intimal elastic lamina (IEL) layer of the coronary arteries. Thickening of the IEL is caused at least in part by emigration of effector cells bearing the CD2 marker such as T cells and NK cells. Clausell et al., *Am. J. Path.*, 142(6):1772–1786 (1993).

These rabbits are maintained on a high fat diet to help accelerate the effects of rejection. As a result of the diet, basal levels of IEL thickening and lesion severity are elevated relative to rabbits fed on a normal diet. Basal levels are assayed in the coronary arteries of the hearts of recipient animals, whereas IEL thickening and lesion severity are assayed in the coronary arteries of the grafted hearts.

Upon examination of vessels of the saline-treated rabbits, a large percentage of the vessels exhibit IEL thickening. Similar evaluation of vessels from the rabbits that receive the inhibitor peptide treatment show that a smaller percentage of the vessels exhibit IEL thickening.

EXAMPLE 6
In Vitro Porcine Allograft Model

A similar study is carried out in vitro using porcine coronary artery endothelial cells (EC; as are present in the IEL) and smooth muscle cells (SMC; as are present in the medial layer of the artery). The two cell types are cultured using a membrane transwell system, with the SMC on the bottom layer in M-199 medium (Gibco Labs.). The SMC are stimulated with 100 ng/ml of interleukin-1β (IL-1β) for 24 hours prior to the start of the assay. Porcine peripheral blood lymphocytes are separated by Ficoll-Hypaque, radiolabeled and incubated overnight (about 18 hours) on the EC.

Transendothelial lymphocyte migration in the IL-1β-stimulated SMC is observed as compared to unstimulated SMC (p<0.05). The inhibitor peptide of Example 5, SEQ ID NO:13, present at 10 μg/ml in the medium reduces lymphocyte migration, whereas the same amount of a control peptide does not reduce migration.

EXAMPLE 7
Experimental Autoimmune Encephalomyetlitis in Mice

Experimental autoimmune encephalomyelitis (EAE) is a demyelinating disease of the central nervous system that can be induced in susceptible strains of mice and rats by immunization with myelin basic protein, proteolipid protein (PLP), or their immunodominant T cell determinants, or by injection of CD4-positive T cell clones specific for those determinants. EAE serves as an animal model of human multiple sclerosis. In both diseases, circulating leukocytes such as T cells and monocytes penetrate the blood/brain barrier and damage myelin, resulting in paralysis.

EAE is induced in female SJL/J mice (8 to 14 weeks old) by immunization on day zero with 50 μg of a peptide corresponding to positions 139–151 of PLP emulsified in a 1:1 mixture of PBS and complete Freund's adjuvant (CFA). Each mouse is injected with 0.2 ml of the adjuvant emulsion subcutaneously (s.c.) at two sites in the hind flank. All mice receive $10^7$ killed *Bordetella pertussis* units in 100 μl and are injected intravenously 24 to 72 hours later.

Mice are observed daily, beginning at day 8 for clinical signs of EAE, and disease is scored on a scale of 0–5 as: 0=no disease; 1=floppy tail; 2=moderate hind limb weakness; 3=paraparesis; 4=paraplegis with moderate forelimb weakness; 5=quadriplegis or premoribund state.

A cyclic inhibitor peptide such as that of SEQ ID NO:12 is administered intraperitoneally at 1 mg/mouse in 0.2 ml of incomplete Freund's adjuvant at days 8 and 9. A control peptide is similarly administered.

Summed or averaged scores for clinical signs are plotted vs. time. The area under the resulting curves is calculated between day 8 and day 35 to calculate percentage inhibition of EAE by a cyclic inhibitor peptide. The percent inhibition is calculated as follows:

% Inhibition = 100 −
(Area of cyclic inhibitor peptide ÷ control area) × 100

Animals treated with a cyclic inhibitor peptide contemplated herein exhibit marked improvement in clinical signs as compared to those animals treated with the control peptide.

EXAMPLE 8
CS-1 Expression in Human Rheumatoid Arthritis

Surgically-obtained synovial specimens from human rheumatoid arthritis (RA) patients are examined microscopically for the expression of the CS-1 peptide portion of fibronectin. Ultrathin sections of tissue are stained by the immunoperoxidase technique using anti-CS-1 antibodies, and are studied using transmission electron microscopy. These studies show that CS-1 is expressed on the lumenal aspect of blood vessel endothelium, on the lumenal plasma membrane. The plasma membrane of synoviocytes in the synovial intimal lining at the interface with the joint space is also stained. The CS-1 peptide portion is not found to be expressed in normal synovium.

Binding studies are carried out using the Jurkat T cell line and frozen RA synovial sections. Jurkat cell adhesion can be inhibited by anti-VLA-4 antibodies or the 10-mer CS-1 peptide portion (500 μg/ml) used as standard here (SEQ ID NO:6), but not with antibodies to VLA-5, VCAM-1-A or VCAM-1-B or a peptide in which the 10-mer sequence was scrambled. Stimulated MOLT-4 cells behaved similarly. These results are reported in Elices et al., *J. Clin. Invest.*, 93:405–416 (January 1994).

A similar inhibition of binding of Jurkat cells to human RA synovial sections and not to normal synovial sections is observed using the cyclic inhibitor peptide of SEQ ID NO:10. That peptide is used at its $IC_{50}$ value shown in Table 1 to be about 253-times less than the $IC_{50}$ value for the standard 10-mer. The absolute value of that $IC_{50}$ value is about 0.6 μmolar.

These results illustrate the importance of the CS-1 peptide portion and VLA-4 in a human chronic immunoinflammatory disease state, rheumatoid arthritis. These results also show that a contemplated inhibitor cell can inhibit the binding of inflammatory cells in this human immunoinflammatory disease state.

Although the present invention has now been described in terms of certain preferred embodiments, and exemplified with respect thereto, one skilled in the art will readily appreciate that various modifications, changes, omissions and substitutions may be made without departing from the spirit thereof.

---

We claim:

1. A cyclic peptide of the formula R-$Xaa^1$-Z-Asp-Phe-Y-$Xaa^2$ wherein

R is
(a) $R^1$ that is (i) absent so that the peptide is terminated by the free α-amine of Xaa or (ii) a $C_1$–$C_4$ acyl moiety, or
(b) $R^2$ that is selected from the group consisting of phenylacetyl, benzoyl, phenylalanyl, tyrosyl, N-$C_1$–$C_4$ acyl phenylalanyl and N-$C_1$–$C_4$ acyl tyrosyl;

the $Xaa^1$ and $Xaa^2$ groups are α-amino acid residues that together form a sulfide or disulfide bond in a chain that contains 3 to about 6 atoms, including at least one sulfur atom between the α-carbons of the two Xaa groups, and in which $Xaa^2$ has a C-terminal carboxamide group, or the C-terminal carboxyl is replaced by hydrogen;

Z is absent, or a peptide selected from the group consisting of Pro-Glu-Leu, Phe-Leu, Glu-Phe-Leu, Pro-Glu-Phe-Leu (SEQ ID NO:2), and Gly-Pro-Glu-Phe-Leu (SEQ ID NO:3); and Y is absent, Pro, or $Y^1$ that is a peptide selected from the group consisting of Pro-Ser, Pro-Ser-Thr and Pro-Ser-Thr-Val (SEQ ID NO:4);

with the provisos that:
(i) R is $R^2$ when Z is absent, and
(ii) $R^2$ is selected from the group consisting of phenylacetyl, benzoyl, N-$C_1$–$C_4$ acyl phenylalanyl and N-$C_1$–$C_4$ acyl tyrosyl when the two Xaa residues are separated by two amino acid residues.

2. The cyclic peptide according to claim 1 wherein $Xaa^1$ and $Xaa^2$ together form a sulfide bond in a chain that contains 3 to about 6 atoms.

3. The cyclic peptide according to claim 1 wherein at least one of $xaa^1$ and $Xaa^2$ is an oxidized cysteine and the other is an oxidized cysteine, homocysteine or pencillamine residue such that $Xaa^1$ and $Xaa^2$ together form a disulfide bond and $Xaa^2$ has a C-terminal carboxamide group.

4. A cyclic peptide of the formula R-Xaa-Z-Asp-Phe-Y-Xaa-$NH_2$
wherein
R is
  (a) $R^1$ that is (i) absent so that the peptide is terminated by the free α-amine of Xaa or (ii) a $C_1$–$C_4$ acyl moiety, or
  (b) $R^2$ that is selected from the group consisting of phenylacetyl, benzoyl, phenylalanyl, tyrosyl, N-$C_1$–$C_4$ acyl phenylalanyl and N-$C_1$–$C_4$ acyl tyrosyl;
at least one Xaa is an oxidized cysteine and the other Xaa is an oxidized cysteine, homocysteine or penicillamine residue such that the two Xaa's together form a disulfide bond;
Z is absent, or a peptide selected from the group consisting of Pro-Glu-Leu, Phe-Leu, Glu-Phe-Leu, Pro-Glu-Phe-Leu (SEQ ID NO:2), and Gly-Pro-Glu-Phe-Leu (SEQ ID NO:3); and
Y is absent, Pro, or $Y^1$ that is a peptide selected from the group consisting of Pro-Ser, Pro-Ser-Thr and Pro-Ser-Thr-Val (SEQ ID NO:4);
with the provisos that:
  (i) R is $R^2$ when Z is absent, and
  (ii) $R^2$ is selected from the group consisting of phenylacetyl, benzoyl, N-$C_1$–$C_4$ acyl phenylalanyl and N-$C_1$–$C_4$ acyl tyrosyl when the two Xaa residues are separated by two amino acid residues.

5. The cyclic peptide according to claim 4 wherein Z is absent.

6. The cyclic peptide according to claim 5 wherein said Y is absent.

7. The cyclic peptide according to claim 4 wherein said Y is absent.

8. The cyclic peptide according to claim 4 wherein R is $R^1$.

9. A cyclic peptide of the formula R-Xaa-$Z^1$-Asp-Phe-Y2-Xaa-$NH_2$
wherein
R is
  (a) $R^1$ that is (i) absent so that the peptide is terminated by the free α-amine of Xaa or (ii) a $C_1$–$C_4$ acyl moiety, or
  (b) $R^2$ that is selected from the group consisting of phenylacetyl, benzoyl, phenylalanyl, tyrosyl, N-$C_1$–$C_4$ acyl phenylalanyl and N-$C_1$–$C_4$ acyl tyrosyl;
at least one Xaa is an oxidized cysteine and the other Xaa is an oxidized cysteine, homocysteine or penicillamine residue such that the two xaa's together form a disulfide bond;
$Z^1$ is absent or Phe-Leu; and
$Y^2$ is absent, Pro, Pro-Ser or Pro-Ser-Thr;
with the provisos that:
  (i) R is $R^2$ when $Z^1$ is absent, and
  (ii) $R^2$ is selected from the group consisting of phenylacetyl, benzoyl, N-$C_1$–$C_4$ acyl phenylalanyl and N-$C_1$–$C_4$ acyl tyrosyl when the two Xaa residues are separated by two amino acid residues.

10. The cyclic peptide according to claim 9 wherein $Z^1$ is Phe-Leu.

11. The cyclic peptide according to claim 9 wherein $Y^2$ is Pro-Ser.

12. The cyclic peptide according to claim 11 wherein $Z^1$ is Phe-Leu.

13. The cyclic peptide according to claim 9 wherein both Xaa residues are oxidized Cys residues.

14. A cyclic peptide of the formula $R^1$-Cys-Phe-Leu-Asp-Phe-$Y^3$-Cys-$NH_2$,
wherein
the two Cys residues are oxidized to form a cystine residue;
$R^1$ is a $C_1$–$C_4$ acyl moiety or absent so that the peptide is terminated by the free α-amine of the oxidized Cys residue; and
$Y^3$ is Pro or Pro-Ser.

15. A cyclic peptide of the formula N-phenylacetyl-Cys-Asp-Phe-Cys-$NH_2$ (SEQ ID NO:7) in which the two cysteines are oxidized to form a disulfide bond-containing cystine residue.

16. A process for treating fibronectin CS1/VLA-4-mediated inflammation that comprises administering to a mammal having said inflammation an inflammation-reducing amount of a cyclic peptide of the formula R-$Xaa^1$-Z-Asp-Phe-Y-$Xaa^2$ wherein
R is
  (a) $R^1$ that is (i) absent so that the peptide is terminated by the free α-amine of Xaa or (ii) a $C_1$–$C_4$ acyl moiety, or
  (b) $R^2$ that is selected from the group consisting of phenylacetyl, benzoyl, phenylalanyl, tyrosyl, N-C1–$C_4$ acyl phenylalanyl and N-C1–$C_4$ acyl tyrosyl;
  the $Xaa^1$ and $Xaa^2$ groups are α-amino acid residues that together form a sulfide or disulfide bond in a chain that contains 3 to about 6 atoms, including at least one sulfur atom between the α-carbons of the two Xaa groups, and in which $Xaa^2$ has a C-terminal carboxamide group, or the C-terminal carboxyl is replaced by hydrogen;
Z is absent, or a peptide selected from the group consisting of Pro-Glu-Leu, Phe-Leu, Glu-Phe-Leu, Pro-Glu-Phe-Leu (SEQ ID NO:2), and Gly-Pro-Glu-Phe-Leu (SEQ ID NO:3); and
Y is absent, Pro, or $Y^1$ that is a peptide selected from the group consisting of Pro-Ser, Pro-Ser-Thr and Pro-Ser-Thr-Val (SEQ ID NO:4);
with the provisos that:
  (i) R is $R^2$ when Z is absent, and
  (ii) $R^2$ is selected from the group consisting of phenylacetyl, benzoyl, N-C1–C4 acyl phenylalanyl and N-C1–C4 acyl tyrosyl when the two Xaa residues are separated by two amino acid residues.

17. The process according to claim 16 wherein said administration is by inhalation.

18. The process according to claim 16 wherein said administration is parenteral.

19. A pharmaceutical composition comprising an inflammation-reducing amount of a cyclic peptide dissolved or dispersed in a pharmaceutically acceptable diluent, said cyclic peptide having the formula R-Xaa¹-Z-Asp-Phe-Y-Xaa² wherein

R is
- (a) $R^1$ that is (i) absent so that the peptide is terminated by the free α-amine of Xaa or (ii) a $C_1$–$C_4$ acyl moiety, or
- (b) $R^2$ that is selected from the group consisting of phenylacetyl, benzoyl, phenylalanyl, tyrosyl, N-$C_1$–$C_4$ acyl phenylalanyl and N-$C_1$–$C_4$ acyl tyrosyl;

the Xaa¹ and Xaa² groups are α-amino acid residues that together form a sulfide or disulfide bond in a chain that contains 3 to about 6 atoms, including at least one sulfur atom between the α-carbons of the two Xaa groups, and in which Xaa² has a C-terminal carboxamide group, or the C-terminal carboxyl is replaced by hydrogen;

Z is absent, or a peptide selected from the group consisting of Pro-Glu-Leu, Phe-Leu, Glu-Phe-Leu, Pro-Glu-Phe-Leu (SEQ ID NO:2), and Gly-Pro-Glu-Phe-Leu (SEQ ID NO:3); and Y is absent, Pro, or $Y^1$ that is a peptide selected from the group consisting of Pro-Ser, Pro-Ser-Thr and Pro-Ser-Thr-Val (SEQ ID NO:4);

with the provisos that:
(i) R is $R^2$ when Z is absent, and
(ii) $R^2$ is selected from the group consisting of phenylacetyl, benzoyl, N-$C_1$–$C_4$ acyl phenylalanyl and N-$C_1$–$C_4$ acyl tyrosyl when the two Xaa residues are separated by two amino acid residues.

20. The pharmaceutical composition according to claim 19 wherein Z is absent.

21. The pharmaceutical composition according to claim 19 wherein Y is absent.

22. The pharmaceutical composition according to claim 19 wherein Z is Phe-Leu and Y is Pro.

23. The pharmaceutical composition according to claim 19 wherein said cyclic peptide is selected from the group consisting of SEQ ID NO'S:7, 10, 12, and 13, and N-phenylacetyl-penicillaminyl-Asp-Phe-Cys-$NH_2$, in which the penicillaminyl and cysteine are oxidized to form a disulfide bond-containing residue (SEQ ID NO:14).

24. A cyclic inhibitor peptide having the following formula:

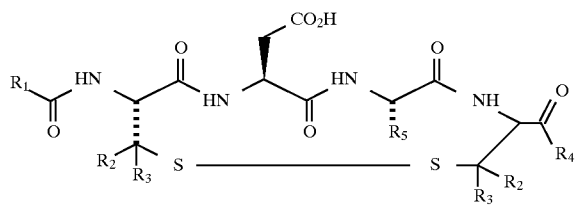

wherein:

$R_1$ is a phenyl or pyridyl group connected by a lower alkyl;

$R_2$ is a H or methyl group;

$R_3$ is a H or methyl group;

$R_4$ is an amine (—$NH_2$), lower alkyl amine, lower alkyl ester or hydroxyl group; and $R_5$ is a phenyl, pyridyl or cyclohexane group connected by a lower alkyl.

25. The cyclic inhibitor peptide of claim 24, wherein $R_1$ is a phenyl methyl group.

26. The cyclic inhibitor peptide of claim 24, wherein $R_4$ is an amine group.

27. The cyclic inhibitor peptide of claim 24, wherein R5 is a phenyl methyl group.

* * * * *

SEQUENCE LISTING ( 1 ) GENERAL INFORMATION:

( i i i ) NUMBER OF SEQUENCES: 33

( 2 ) INFORMATION FOR SEQ ID NO:1:

( i ) SEQUENCE CHARACTERISTICS:
        ( A ) LENGTH: 5 amino acids
        ( B ) TYPE: amino acid
        ( D ) TOPOLOGY: circular ( i i ) MOLECULE TYPE: peptide ( i x ) FEATURE:
        ( A ) NAME/KEY: Peptide
        ( B ) LOCATION: 4
        ( D ) OTHER INFORMATION: /note= "Xaa is (ThioP)."

( x i ) SEQUENCE DESCRIPTION: SEQ ID NO:1:

Arg  Cys  Asp  Xaa  Cys
    1                            5

( 2 ) INFORMATION FOR SEQ ID NO:2:

( i ) SEQUENCE CHARACTERISTICS:
        ( A ) LENGTH: 4 amino acids
        ( B ) TYPE: amino acid (D) TOPOLOGY: linear (ii) MOLECULE TYPE: peptide (xi) SEQUENCE DESCRIPTION: SEQ ID NO:2:

Pro Glu Phe Leu
1

(2) INFORMATION FOR SEQ ID NO:3:

(i) SEQUENCE CHARACTERISTICS:
      (A) LENGTH: 5 amino acids
      (B) TYPE: amino acid
      (D) TOPOLOGY: linear (ii) MOLECULE TYPE: peptide (xi) SEQUENCE DESCRIPTION: SEQ ID NO:3:

Gly Pro Glu Phe Leu
1                 5

(2) INFORMATION FOR SEQ ID NO:4:

(i) SEQUENCE CHARACTERISTICS:
      (A) LENGTH: 4 amino acids
      (B) TYPE: amino acid
      (D) TOPOLOGY: linear (ii) MOLECULE TYPE: peptide (xi) SEQUENCE DESCRIPTION: SEQ ID NO:4:

Pro Ser Thr Val
1

(2) INFORMATION FOR SEQ ID NO:5:

(i) SEQUENCE CHARACTERISTICS:
      (A) LENGTH: 25 amino acids
      (B) TYPE: amino acid
      (D) TOPOLOGY: linear (ii) MOLECULE TYPE: peptide (xi) SEQUENCE DESCRIPTION: SEQ ID NO:5:

Asp Glu Leu Pro Gln Leu Val Thr Leu Pro His Pro Asn Leu His Gly
1            5                        10                      15

Pro Glu Ile Leu Asp Val Pro Ser Thr
          20                       25

(2) INFORMATION FOR SEQ ID NO:6:

(i) SEQUENCE CHARACTERISTICS:
      (A) LENGTH: 10 amino acids
      (B) TYPE: amino acid
      (D) TOPOLOGY: linear (ii) MOLECULE TYPE: peptide (xi) SEQUENCE DESCRIPTION: SEQ ID NO:6:

Gly Pro Glu Ile Leu Asp Val Pro Ser Thr
1                 5                        10

(2) INFORMATION FOR SEQ ID NO:7:

(i) SEQUENCE CHARACTERISTICS:
      (A) LENGTH: 4 amino acids
      (B) TYPE: amino acid
      (D) TOPOLOGY: circular (i i) MOLECULE TYPE: peptide (i x) FEATURE:
    (A) NAME/KEY: Peptide
    (B) LOCATION: 1
    (D) OTHER INFORMATION: /note= "A phenylacetyl group is attached to the amine group."

(i x) FEATURE:
    (A) NAME/KEY: Peptide
    (B) LOCATION: 4
    (D) OTHER INFORMATION: /note= "The hydroxy group attached to the carbonyl group is replaced by an amine group."

(x i) SEQUENCE DESCRIPTION: SEQ ID NO:7:

Cys Asp Phe Cys
1

(2) INFORMATION FOR SEQ ID NO:8:

(i) SEQUENCE CHARACTERISTICS:
        (A) LENGTH: 4 amino acids
        (B) TYPE: amino acid
        (D) TOPOLOGY: circular (i i) MOLECULE TYPE: peptide (i x) FEATURE:
        (A) NAME/KEY: Peptide
        (B) LOCATION: 4
        (D) OTHER INFORMATION: /note= "The hydroxy group attached to the carbonyl group is replaced by an amine group."

(x i) SEQUENCE DESCRIPTION: SEQ ID NO:8:

Cys Asp Phe Cys
1

(2) INFORMATION FOR SEQ ID NO:9:

(i) SEQUENCE CHARACTERISTICS:
        (A) LENGTH: 12 amino acids
        (B) TYPE: amino acid
        (D) TOPOLOGY: linear (i i) MOLECULE TYPE: peptide (x i) SEQUENCE DESCRIPTION: SEQ ID NO:9:

Leu His Gly Pro Glu Ile Leu Asp Val Pro Ser Thr
1               5                   10

(2) INFORMATION FOR SEQ ID NO:10:

(i) SEQUENCE CHARACTERISTICS:
        (A) LENGTH: 7 amino acids
        (B) TYPE: amino acid
        (D) TOPOLOGY: circular (i i) MOLECULE TYPE: peptide (i x) FEATURE:
        (A) NAME/KEY: Peptide
        (B) LOCATION: 7
        (D) OTHER INFORMATION: /note= "The hydroxy group attached to the carbonyl group is replaced by an amine group."

(x i) SEQUENCE DESCRIPTION: SEQ ID NO:10:

Cys Phe Leu Asp Phe Pro Cys
1               5

( 2 ) INFORMATION FOR SEQ ID NO:11:

( i ) SEQUENCE CHARACTERISTICS:
  ( A ) LENGTH: 7 amino acids
  ( B ) TYPE: amino acid
  ( D ) TOPOLOGY: circular ( i i ) MOLECULE TYPE: peptide ( i x ) FEATURE:
  ( A ) NAME/KEY: Peptide
  ( B ) LOCATION: 1
  ( D ) OTHER INFORMATION: /note= "An acetyl group is attached to the amine group."

( i x ) FEATURE:
  ( A ) NAME/KEY: Peptide
  ( B ) LOCATION: 7
  ( D ) OTHER INFORMATION: /note= "The hydroxy group attached to the carbonyl group is replaced by an amine group."

( x i ) SEQUENCE DESCRIPTION: SEQ ID NO:11:

Cys Phe Leu Asp Phe Pro Cys
1      5

( 2 ) INFORMATION FOR SEQ ID NO:12:

( i ) SEQUENCE CHARACTERISTICS:
  ( A ) LENGTH: 6 amino acids
  ( B ) TYPE: amino acid
  ( D ) TOPOLOGY: circular ( i i ) MOLECULE TYPE: peptide ( i x ) FEATURE:
  ( A ) NAME/KEY: Peptide
  ( B ) LOCATION: 6
  ( D ) OTHER INFORMATION: /note= "The hydroxy group attached to the carbonyl group is replaced by an amine group."

( x i ) SEQUENCE DESCRIPTION: SEQ ID NO:12:

Phe Cys Asp Phe Pro Cys
1     5

( 2 ) INFORMATION FOR SEQ ID NO:13:

( i ) SEQUENCE CHARACTERISTICS:
  ( A ) LENGTH: 8 amino acids
  ( B ) TYPE: amino acid
  ( D ) TOPOLOGY: circular ( i i ) MOLECULE TYPE: peptide ( i x ) FEATURE:
  ( A ) NAME/KEY: Peptide
  ( B ) LOCATION: 8
  ( D ) OTHER INFORMATION: /note= "The hydroxy group attached to the carbonyl group is replaced by an amine group."

( x i ) SEQUENCE DESCRIPTION: SEQ ID NO:13:

Cys Phe Leu Asp Phe Pro Ser Cys
1      5

( 2 ) INFORMATION FOR SEQ ID NO:14:

( i ) SEQUENCE CHARACTERISTICS:
  ( A ) LENGTH: 4 amino acids
  ( B ) TYPE: amino acid
  ( D ) TOPOLOGY: circular ( i i ) MOLECULE TYPE: peptide ( i x ) FEATURE:
    ( A ) NAME/KEY: Peptide
    ( B ) LOCATION: 1
    ( D ) OTHER INFORMATION: /note= "A phenylacetyl group is
        attached to the amine group."

( i x ) FEATURE:
    ( A ) NAME/KEY: Peptide
    ( B ) LOCATION: 1
    ( D ) OTHER INFORMATION: /note= "Xaa is penicillaminyl."

( i x ) FEATURE:
    ( A ) NAME/KEY: Peptide
    ( B ) LOCATION: 4
    ( D ) OTHER INFORMATION: /note= "The hydroxy group attached
        to the carbonyl group is replaced by an amine
        group."

( x i ) SEQUENCE DESCRIPTION: SEQ ID NO:14:

Xaa  Asp  Phe  Cys
1

( 2 ) INFORMATION FOR SEQ ID NO:15:

( i ) SEQUENCE CHARACTERISTICS:
        ( A ) LENGTH: 9 amino acids
        ( B ) TYPE: amino acid
        ( D ) TOPOLOGY: circular ( i i ) MOLECULE TYPE: peptide ( i x ) FEATURE:
        ( A ) NAME/KEY: Peptide
        ( B ) LOCATION: 9
        ( D ) OTHER INFORMATION: /note= "The hydroxy group attached
        to the carbonyl group is replaced by an amine
        group."

( x i ) SEQUENCE DESCRIPTION: SEQ ID NO:15:

Cys  Phe  Leu  Asp  Phe  Pro  Ser  Thr  Cys
1                           5

( 2 ) INFORMATION FOR SEQ ID NO:16:

( i ) SEQUENCE CHARACTERISTICS:
        ( A ) LENGTH: 9 amino acids
        ( B ) TYPE: amino acid
        ( D ) TOPOLOGY: circular ( i i ) MOLECULE TYPE: peptide ( i x ) FEATURE:
        ( A ) NAME/KEY: Peptide
        ( B ) LOCATION: 9
        ( D ) OTHER INFORMATION: /note= "The hydroxy group attached
        to the carbonyl group is replaced by an amine
        group."

( x i ) SEQUENCE DESCRIPTION: SEQ ID NO:16:

Cys  Pro  Glu  Phe  Leu  Asp  Phe  Pro  Cys
1                           5

( 2 ) INFORMATION FOR SEQ ID NO:17:

( i ) SEQUENCE CHARACTERISTICS:
        ( A ) LENGTH: 5 amino acids
        ( B ) TYPE: amino acid
        ( D ) TOPOLOGY: circular ( i i ) MOLECULE TYPE: peptide ( i x ) FEATURE:
        ( A ) NAME/KEY: Peptide (B) LOCATION: 1
(D) OTHER INFORMATION: /note= "An acetyl group is attached to the amine group."

(ix) FEATURE:
(A) NAME/KEY: Peptide
(B) LOCATION: 5
(D) OTHER INFORMATION: /note= "The hydroxy group attached to the carbonyl group is replaced by an amine group."

(xi) SEQUENCE DESCRIPTION: SEQ ID NO:17:

Phe Cys Asp Phe Cys
1               5

(2) INFORMATION FOR SEQ ID NO:18:

(i) SEQUENCE CHARACTERISTICS:
(A) LENGTH: 5 amino acids
(B) TYPE: amino acid
(D) TOPOLOGY: linear (ii) MOLECULE TYPE: peptide (ix) FEATURE:
(A) NAME/KEY: Peptide
(B) LOCATION: 1
(D) OTHER INFORMATION: /note= "The amino-terminus has an acetyl group."

(ix) FEATURE:
(A) NAME/KEY: Peptide
(B) LOCATION: 5
(D) OTHER INFORMATION: /note= "The carboxy-terminus is a carboxamide."

(xi) SEQUENCE DESCRIPTION: SEQ ID NO:18:

Phe Cys Asp Phe Cys
1               5

(2) INFORMATION FOR SEQ ID NO:19:

(i) SEQUENCE CHARACTERISTICS:
(A) LENGTH: 10 amino acids
(B) TYPE: amino acid
(D) TOPOLOGY: circular (ii) MOLECULE TYPE: peptide (ix) FEATURE:
(A) NAME/KEY: Peptide
(B) LOCATION: 10
(D) OTHER INFORMATION: /note= "The hydroxy group attached to the carbonyl group is replaced by an amine group."

(xi) SEQUENCE DESCRIPTION: SEQ ID NO:19:

Cys Pro Glu Phe Leu Asp Phe Pro Ser Cys
1               5                   10

(2) INFORMATION FOR SEQ ID NO:20:

(i) SEQUENCE CHARACTERISTICS:
(A) LENGTH: 8 amino acids
(B) TYPE: amino acid
(D) TOPOLOGY: circular (ii) MOLECULE TYPE: peptide (ix) FEATURE:
(A) NAME/KEY: Peptide
(B) LOCATION: 8
(D) OTHER INFORMATION: /note= "The hydroxy group attached to the carbonyl group is replaced by an amine group."

(x i) SEQUENCE DESCRIPTION: SEQ ID NO:20:

Cys Glu Phe Leu Asp Phe Pro Cys
1               5

(2) INFORMATION FOR SEQ ID NO:21:

(i) SEQUENCE CHARACTERISTICS:
        (A) LENGTH: 10 amino acids
        (B) TYPE: amino acid
        (D) TOPOLOGY: circular (i i) MOLECULE TYPE: peptide (i x) FEATURE:
        (A) NAME/KEY: Peptide
        (B) LOCATION: 10
        (D) OTHER INFORMATION: /note= "The hydroxy group attached
            to the carbonyl group is replaced by an amine
            group."

(x i) SEQUENCE DESCRIPTION: SEQ ID NO:21:

Cys Phe Leu Asp Phe Pro Ser Thr Val Cys
1               5                   10

(2) INFORMATION FOR SEQ ID NO:22:

(i) SEQUENCE CHARACTERISTICS:
        (A) LENGTH: 10 amino acids
        (B) TYPE: amino acid
        (D) TOPOLOGY: circular (i i) MOLECULE TYPE: peptide (i x) FEATURE:
        (A) NAME/KEY: Peptide
        (B) LOCATION: 10
        (D) OTHER INFORMATION: /note= "The hydroxy group attached
            to the carbonyl group is replaced by an amine
            group."

(x i) SEQUENCE DESCRIPTION: SEQ ID NO:22:

Cys Glu Phe Leu Asp Phe Pro Ser Thr Cys
1               5                   10

(2) INFORMATION FOR SEQ ID NO:23:

(i) SEQUENCE CHARACTERISTICS:
        (A) LENGTH: 9 amino acids
        (B) TYPE: amino acid
        (D) TOPOLOGY: circular (i i) MOLECULE TYPE: peptide (i x) FEATURE:
        (A) NAME/KEY: Peptide
        (B) LOCATION: 9
        (D) OTHER INFORMATION: /note= "The hydroxy group attached
            to the carbonyl group is replaced by an amine
            group."

(x i) SEQUENCE DESCRIPTION: SEQ ID NO:23:

Cys Gly Pro Glu Phe Leu Asp Phe Cys
1               5

(2) INFORMATION FOR SEQ ID NO:24:

(i) SEQUENCE CHARACTERISTICS:
        (A) LENGTH: 9 amino acids
        (B) TYPE: amino acid
        (D) TOPOLOGY: circular ( i i ) MOLECULE TYPE: peptide ( i x ) FEATURE:
    ( A ) NAME/KEY: Peptide
    ( B ) LOCATION: 9
    ( D ) OTHER INFORMATION: /note= "The hydroxy group attached
        to the carbonyl group is replaced by an amine
        group."

( x i ) SEQUENCE DESCRIPTION: SEQ ID NO:24:

```
Cys  Glu  Phe  Leu  Asp  Phe  Pro  Ser  Cys
 1                   5
```

( 2 ) INFORMATION FOR SEQ ID NO:25:

( i ) SEQUENCE CHARACTERISTICS:
        ( A ) LENGTH: 5 amino acids
        ( B ) TYPE: amino acid
        ( D ) TOPOLOGY: circular ( i i ) MOLECULE TYPE: peptide ( i x ) FEATURE:
    ( A ) NAME/KEY: Peptide
    ( B ) LOCATION: 5
    ( D ) OTHER INFORMATION: /note= "The hydroxy group attached
        to the carbonyl group is replaced by an amine
        group."

( x i ) SEQUENCE DESCRIPTION: SEQ ID NO:25:

```
Phe  Cys  Asp  Phe  Cys
 1                   5
```

( 2 ) INFORMATION FOR SEQ ID NO:26:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: peptide ( i x ) FEATURE:
    ( A ) NAME/KEY: Peptide
    ( B ) LOCATION: 10
    ( D ) OTHER INFORMATION: /note= "The carboxy-terminus is a
        carboxamide."

( x i ) SEQUENCE DESCRIPTION: SEQ ID NO:26:

```
Ile  Leu  Asp  Val  Pro  Ile  Leu  Asp  Val  Pro
 1                   5                        10
```

( 2 ) INFORMATION FOR SEQ ID NO:27:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( i x ) FEATURE:
    ( A ) NAME/KEY: Peptide
    ( B ) LOCATION: 5
    ( D ) OTHER INFORMATION: /note= "The carboxy-terminus is a
        carboxamide."

( x i ) SEQUENCE DESCRIPTION: SEQ ID NO:27:

```
Ile  Leu  Asp  Phe  Pro
 1                   5
```

( 2 ) INFORMATION FOR SEQ ID NO:28:

( i ) SEQUENCE CHARACTERISTICS:
    ( A ) LENGTH: 5 amino acids
    ( B ) TYPE: amino acid
    ( D ) TOPOLOGY: circular ( i i ) MOLECULE TYPE: peptide ( i x ) FEATURE:
    ( A ) NAME/KEY: Peptide
    ( B ) LOCATION: 5
    ( D ) OTHER INFORMATION: /note= "The hydroxy group attached
        to the carbonyl group is replaced by an amine
        group."

( x i ) SEQUENCE DESCRIPTION: SEQ ID NO:28:

Cys  Leu  Asp  Phe  Cys
  1                   5

( 2 ) INFORMATION FOR SEQ ID NO:29:

( i ) SEQUENCE CHARACTERISTICS:
    ( A ) LENGTH: 5 amino acids
    ( B ) TYPE: amino acid
    ( D ) TOPOLOGY: circular ( i i ) MOLECULE TYPE: peptide ( i x ) FEATURE:
    ( A ) NAME/KEY: Peptide
    ( B ) LOCATION: 1
    ( D ) OTHER INFORMATION: /note= "An acetyl group is attached
        to the amine group."

( i x ) FEATURE:
    ( A ) NAME/KEY: Peptide
    ( B ) LOCATION: 5
    ( D ) OTHER INFORMATION: /note= "The hydroxy group attached
        to the carbonyl group is replaced by an amine
        group."

( x i ) SEQUENCE DESCRIPTION: SEQ ID NO:29:

Phe  Cys  Asp  Cys  Pro
  1                   5

( 2 ) INFORMATION FOR SEQ ID NO:30:

( i ) SEQUENCE CHARACTERISTICS:
    ( A ) LENGTH: 5 amino acids
    ( B ) TYPE: amino acid
    ( D ) TOPOLOGY: circular ( i i ) MOLECULE TYPE: peptide ( i x ) FEATURE:
    ( A ) NAME/KEY: Peptide
    ( B ) LOCATION: 5
    ( D ) OTHER INFORMATION: /note= "The carboxy-terminus is a
        carboxamide."

( x i ) SEQUENCE DESCRIPTION: SEQ ID NO:30:

Phe  Cys  Asp  Cys  Pro
  1                   5

( 2 ) INFORMATION FOR SEQ ID NO:31:

( i ) SEQUENCE CHARACTERISTICS:
    ( A ) LENGTH: 5 amino acids
    ( B ) TYPE: amino acid
    ( D ) TOPOLOGY: linear ( i i ) MOLECULE TYPE: peptide -continued

```
      ( i x ) FEATURE:
              ( A ) NAME/KEY: Peptide
              ( B ) LOCATION: 5
              ( D ) OTHER INFORMATION: /note= "The carboxy-terminus is a
                    carboxamide."

( x i ) SEQUENCE DESCRIPTION: SEQ ID NO:31:

Ser  Phe  Asp  Phe  Ser
      1                   5

( 2 ) INFORMATION FOR SEQ ID NO:32:

( i ) SEQUENCE CHARACTERISTICS:
              ( A ) LENGTH: 5 amino acids
              ( B ) TYPE: amino acid
              ( D ) TOPOLOGY: circular ( i i ) MOLECULE TYPE: peptide ( i x ) FEATURE:
              ( A ) NAME/KEY: Peptide
              ( B ) LOCATION: 1
              ( D ) OTHER INFORMATION: /note= "An acyl group is attached
                    to the amine group."

( i x ) FEATURE:
              ( A ) NAME/KEY: Peptide
              ( B ) LOCATION: 5
              ( D ) OTHER INFORMATION: /note= "The hydroxy group attached
                    to the carbonyl group is replaced by an amine
                    group."

( x i ) SEQUENCE DESCRIPTION: SEQ ID NO:32:

Cys  Leu  Asp  Phe  Cys
      1                   5

( 2 ) INFORMATION FOR SEQ ID NO:33:

( i ) SEQUENCE CHARACTERISTICS:
              ( A ) LENGTH: 9 amino acids
              ( B ) TYPE: amino acid
              ( D ) TOPOLOGY: circular ( i i ) MOLECULE TYPE: peptide ( i x ) FEATURE:
              ( A ) NAME/KEY: Peptide
              ( B ) LOCATION: 9
              ( D ) OTHER INFORMATION: /note= "The hydroxy group attached
                    to the carbonyl group is replaced by an amine
                    group."

( x i ) SEQUENCE DESCRIPTION: SEQ ID NO:33:

Cys  Pro  Glu  Leu  Asp  Phe  Pro  Ser  Cys
      1                   5
```